United States Patent [19]
Cahalan et al.

[11] Patent Number: 5,397,702
[45] Date of Patent: Mar. 14, 1995

[54] ASSAY FOR AND TREATMENT OF AUTOIMMUNE DISEASES

[75] Inventors: Michael D. Cahalan; Kanianthara G. Chandy, both of Laguna Beach, Calif.; Stephan Grissmer, Irvine, Calif; Sanjiv Ghanshani, Chino, Hills, Calif.; George A. Gutman, Costa Mesa, Calif.; Brent A. Dethlefs, Fountain Valley, Calif.

[73] Assignee: The Regents of the University of California, Oakland, Calif.

[21] Appl. No.: 955,916

[22] Filed: Oct. 2, 1992

Related U.S. Application Data

[63] Continuation-in-part of Ser. No. 668,609, Mar. 13, 1991, abandoned, which is a continuation-in-part of Ser. No. 319,499, Mar. 6, 1989, abandoned.

[30] Foreign Application Priority Data

Mar. 5, 1990 [WO] WIPO ................. PCT/US90/01197

[51] Int. Cl.$^6$ ............................................ C12P 21/06
[52] U.S. Cl. ................................ 435/69.1; 435/172.3; 435/6; 536/23.1; 536/23.5; 536/25.5
[58] Field of Search .................... 536/23.1, 23.5, 25.3; 530/350, 839; 424/570; 435/69.1, 172.3, 6; 436/149, 506, 501, 811, 815

[56] References Cited

FOREIGN PATENT DOCUMENTS 8906967 8/1989 WIPO .
8906968 8/1989 WIPO .

OTHER PUBLICATIONS

Till, et al., *Biological Abstracts*, vol. 87, No. 4, p. AB-167 (1989).
Katz, et al., *Biological Abstracts*, vol. 85, No. 7, p. AB-651 (1988).
Tempel, et al., *Nature* 332, 837 (1988).
Baumann, et al., *The EMBO Journal* 7, 2457 (1988).
McKinnon, *The Journal of Biological Chemistry* 264, 8230 (1989).
Frech, et al., *Nature* 642, 340 (1989).
Miller, *Trends Neurosci.* 13, No. 6, 197 (1990).
Cook *TIPS*, 9 Elsevier Publications 21–28 (1988).
Robertson, et al., *Jour. Medicinal Chem.* 33 No. 6, 1529 (1990).
Swanson, et al., *Neuron* 4, 929 (1990).
Chandy, et al., *European J. Immunol.* 20, 747 (1990).
Ghanshani, et al., Abstract submitted for the Biophysics Conference in Vancouver, July 29 to Aug. 3, 1990.
Gupta, et al., *Cell Immunol.* 104 (2), 290 (1987) Abstract.
Chandy, et al., *Science* 247, 973 (1990).
Chandy, et al., Abstract Biophysical Meeting, Baltimore, Md., Feb. (1990).
Grissmer, et al., Abstract, Tenth International Biophysical Congress, Vancouver, Canada 29 July to 3 Aug. 1990.
Douglass, et al., *J. Immunol.* 144, 4841 (1990).
Stühmer, et al., *EMBO J* 8, 3235 (1989).
Swanson, et al., *Biophysical Journal* 57, 211a (1990).
McCormack, et al., *Proc. Natl. Acad. Sci. USA* 87, 5227 (1990).
Ribera, *Neuron* 5, 691 (1990).
Chandy, et al., *Biophysical Journal* 61, Abstract #1484 (1992).
Grissmer, et al., *Proc. Natl. Acad. Sci. USA* 87, 9411 (1990).
Douglass, et al., *The Journal of Immunology* 144, 4841 (1990).
Luneau, et al., *Pro. Natl. Acad. Sci. USA* 88, 3932 (1991).
Murakami, et al., *FASEB Journal* 4, Abstract #2404 (1990).

(List continued on next page.)

*Primary Examiner*—Christine M. Nucker
*Assistant Examiner*—Laurie Scheiner
*Attorney, Agent, or Firm*—Walter H. Dreger

[57] ABSTRACT

This disclosure relates to the general diagnosis and treatment of autoimmune diseases with materials identified in assays based upon the finding herein that such diseases manifest by elevated numbers of type 1 K+ channels in abnormal CD4−CD8−T cells.

5 Claims, 15 Drawing Sheets

OTHER PUBLICATIONS

Chandy, et al., *American Rheumatism Association*, 53rd Annual Scientific Meeting, Ohio, (1989).
Chandy, et al., *Society for Neuroscience Abstracts* 15, #220.1, (1989).
Grissmer, et al., *J. Immunol.* 145, 2105 (1990).
Mathew, et al., *Society for Neuroscience Abstracts* 15, Abstract #230.12 (1989).
Ramaswami, et al., *Mol. Cell. Neurosciences*, 1, 214 (1990).
Yokoyama, et al., *FEBS Letters* 259, 37 (1989).
Grupe, et al., *The EMBO Journal* 9, (1990).
Theofilopoulous, et al., *Adv. Immunol.* 37, 269 (1985).
Shapiro, et al., *Biophys. J.* 53, 550a (1988).
Lewis, et al., *Science* 239, 771 (1988).
DeCoursey, et al., *J. Gen. Physiol.* 89, 405 (1987).
Chandy, et al., *Science* 233, 1197 (1986).
Grissmer, et al., *J. Immunology* 141, 1137 (1988).
DeCoursey, et al., *Nature* 307, 465 (1984).
Wofsy and Seaman, *J. Exp. Med.* 161, 378 (1985).
Wofsy, et al., *J. Immunol.* 134, 852 (1985).
Santoro, et al., *J. Exp. Med.* 167, 1713 (1988).
Waldor, et al., *Science* 227, 415 (1985).
Ranges, et al., *J. Exp. Med.* 162, 1105 (1985).
Christadoss and Dauphinee, *J. Immunol.* 136, 2437 (1986).
Wofsy, *J. Immunol.* 136, 4554 (1986).
Sainis and Datta, *J. Immunol.* 140, 2215 (1988).
Shivakumar, et al., *FASEB J.* 3, A492 (No. 1548) (Feb., 1989).
Datta, *J. Exp. Med.* 165, 1252 (1987).
DeCoursey, et al., *Nature* 307, 465 (1984).
Miller, et al., *J. Immunol.* 140, 52 (1988).
Koike, et al., *Diabetes* 36, 539 (1987).
Yokoyama et al, FEBS Letters, vol. 259, No. 1, 37–42, Dec. 1989, "Potassium Channels from NG 108-15 Neuroblastoma–Glioma Hybrid Cells".
Ohara et al, Proc. Natl. Acad. Sci USA, vol. 86 pp. 5673–5677, Aug. 1989, "One-Sided Polymerase Chain Reaction: The Amplification of CDNA".
Luneau et al, Proc. Natl. Acad. Sci USA, vol. 88, pp. 3932–3936, May 1991, "Alternative Splicing Contributes to K+ Channel Diversity in the Mammalian Central Nervous System".
Rettig et al, The EMBO Journal, vol. 11, No. 7, pp. 2473–2486, 1992.

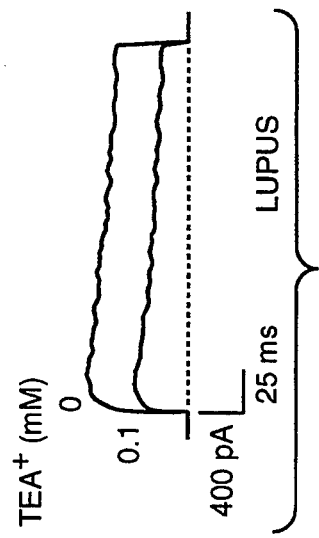
FIG._1A-1
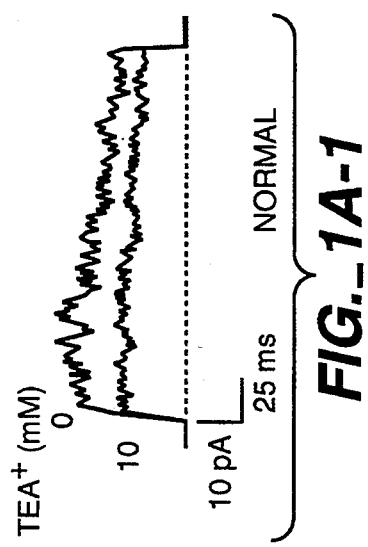
FIG._1B-1
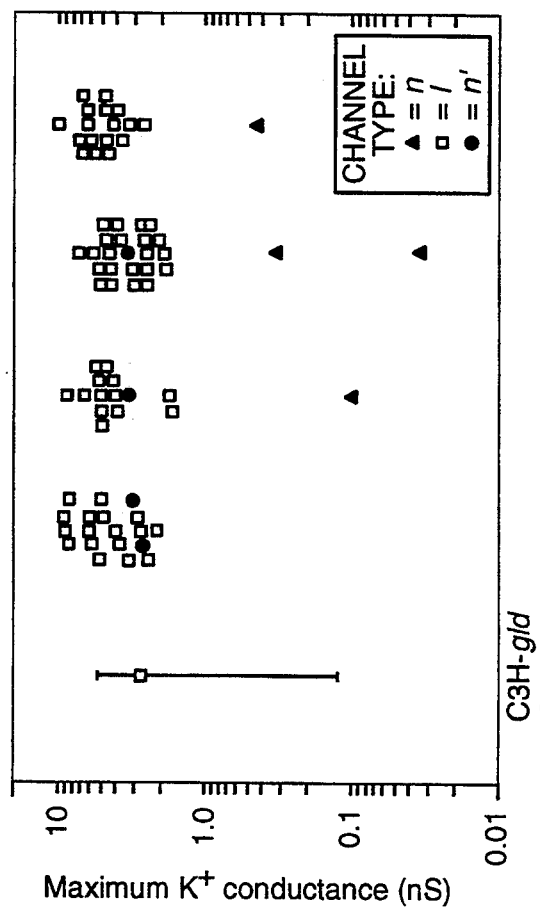
FIG._1A-2
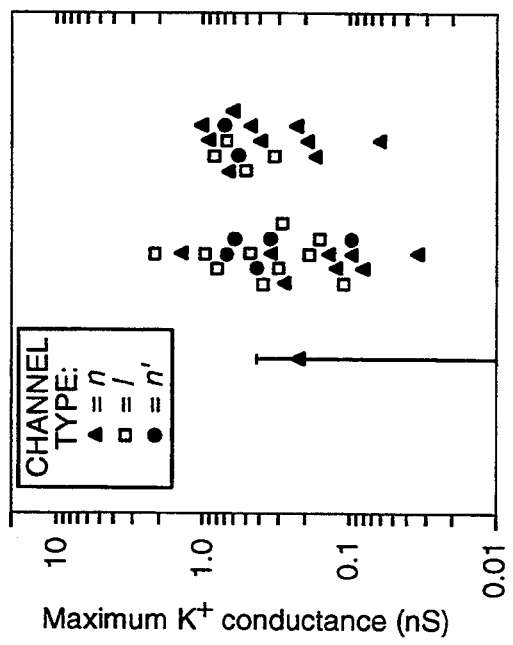
FIG._1B-2

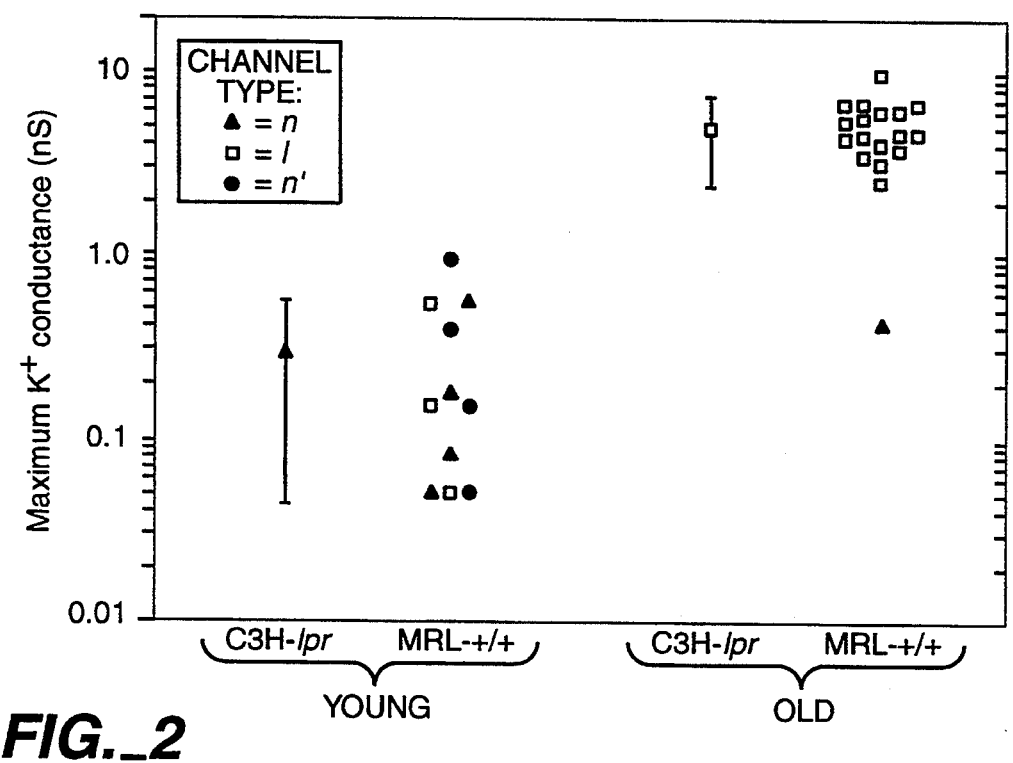
FIG._2
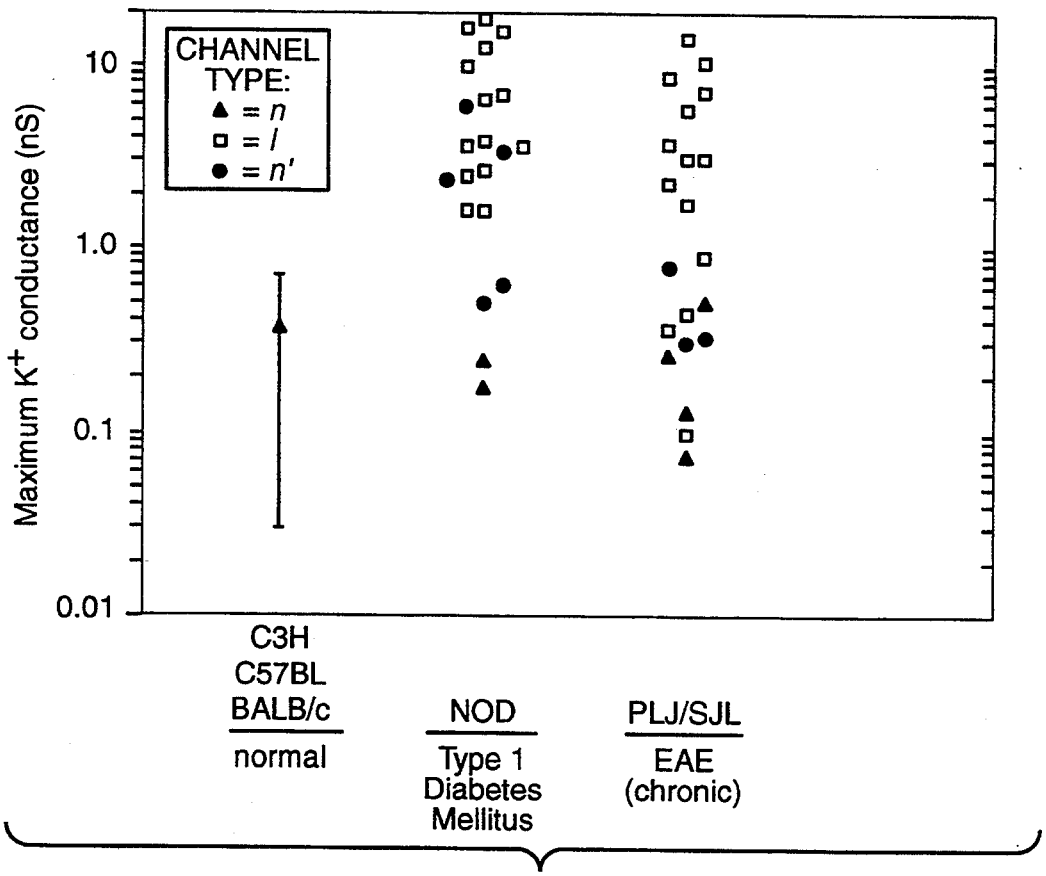
FIG._3

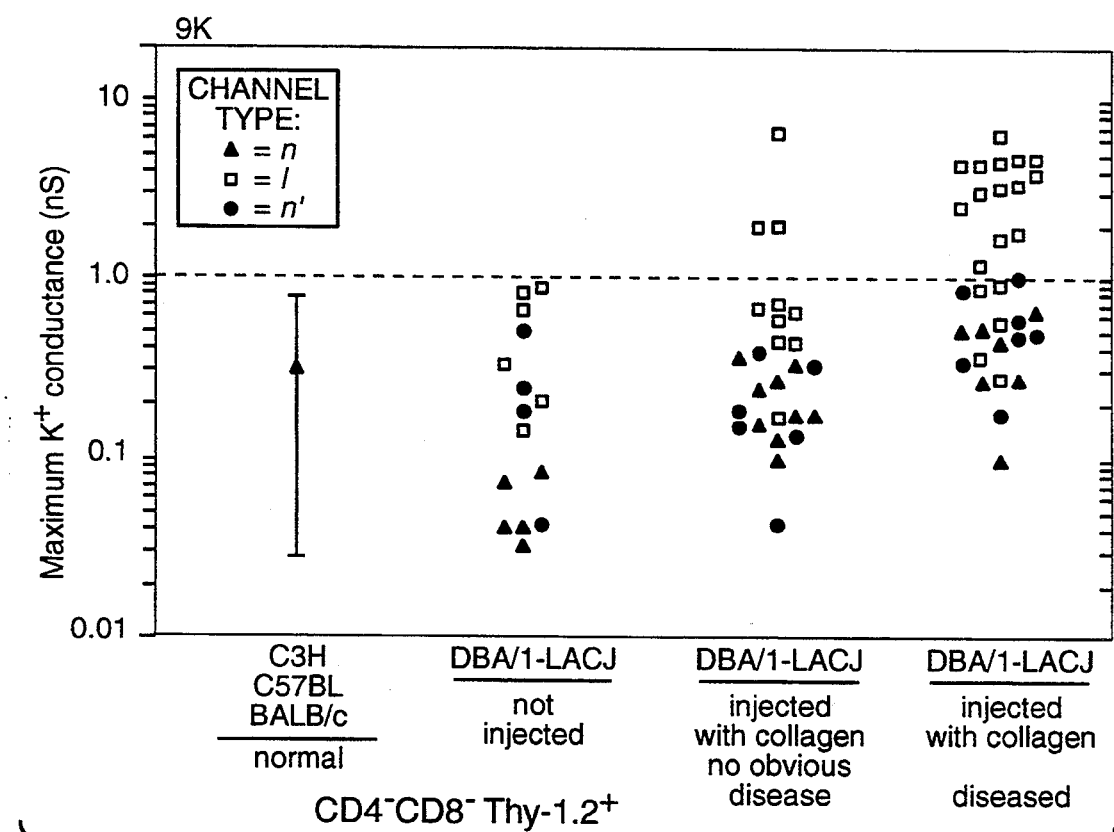
FIG._4A
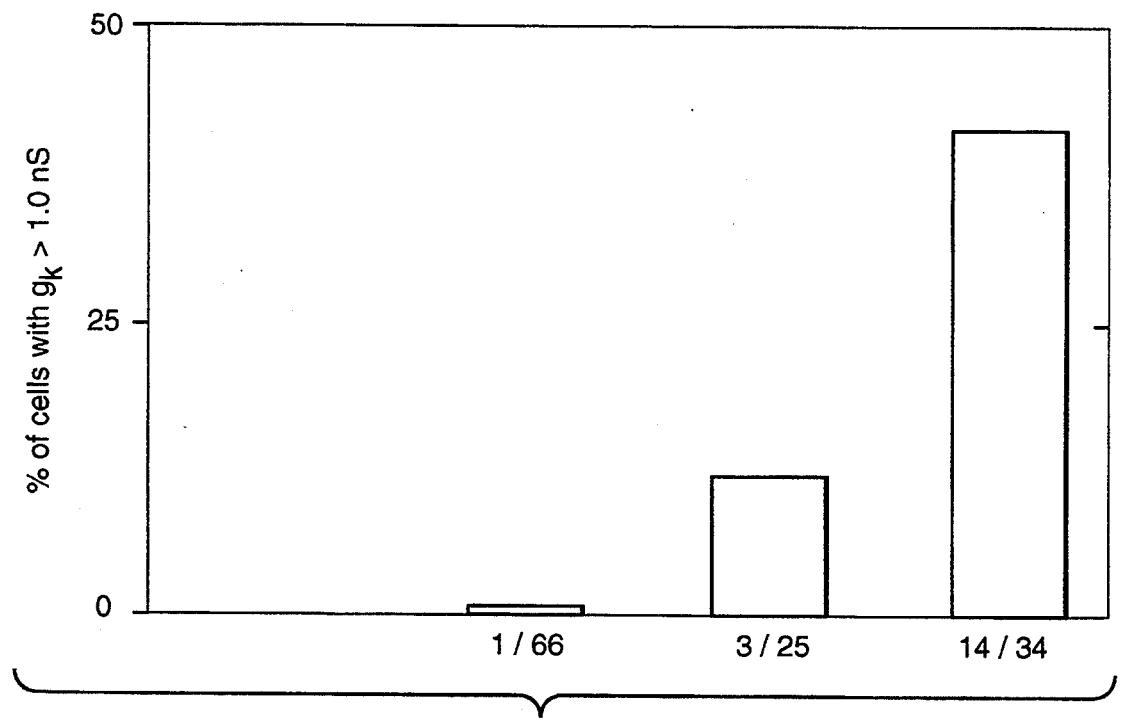
FIG._4B

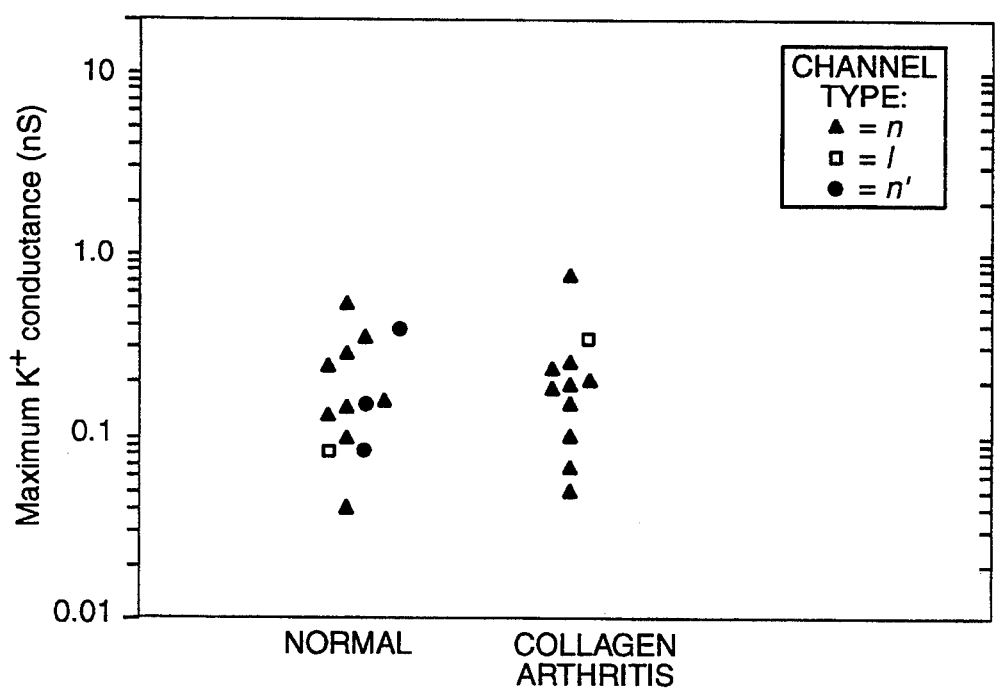
FIG._5A
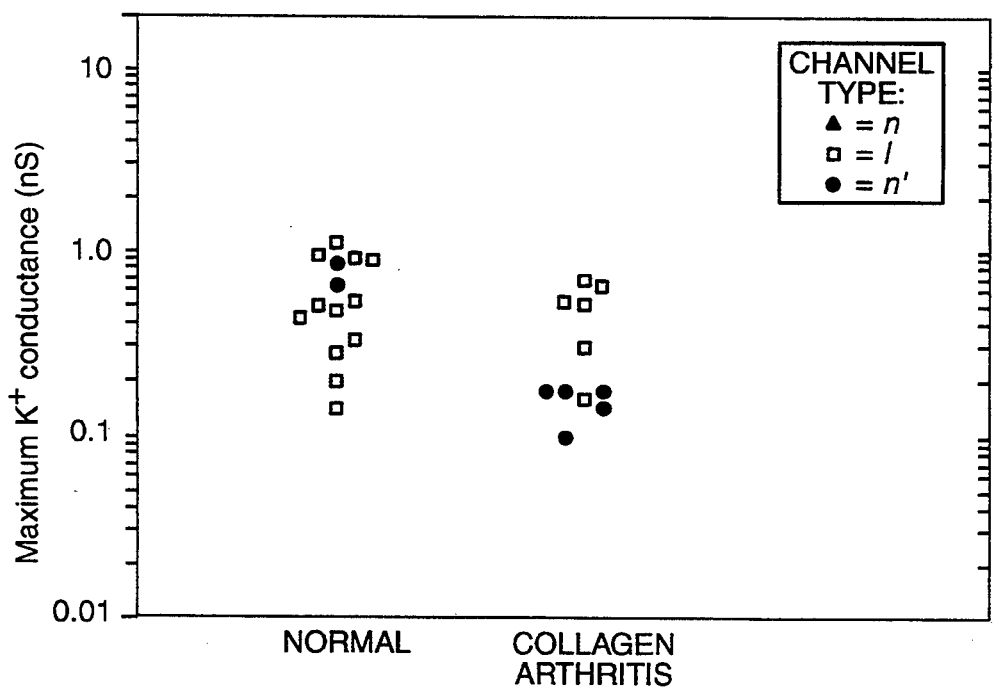
FIG._5B

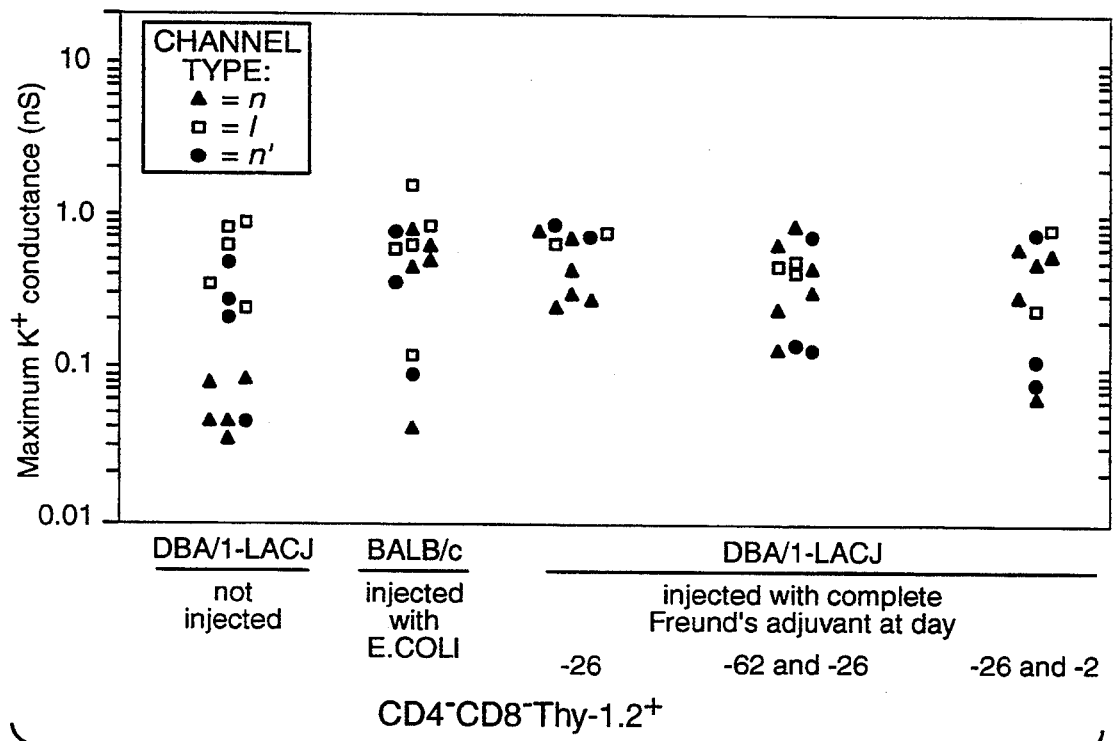
FIG._6
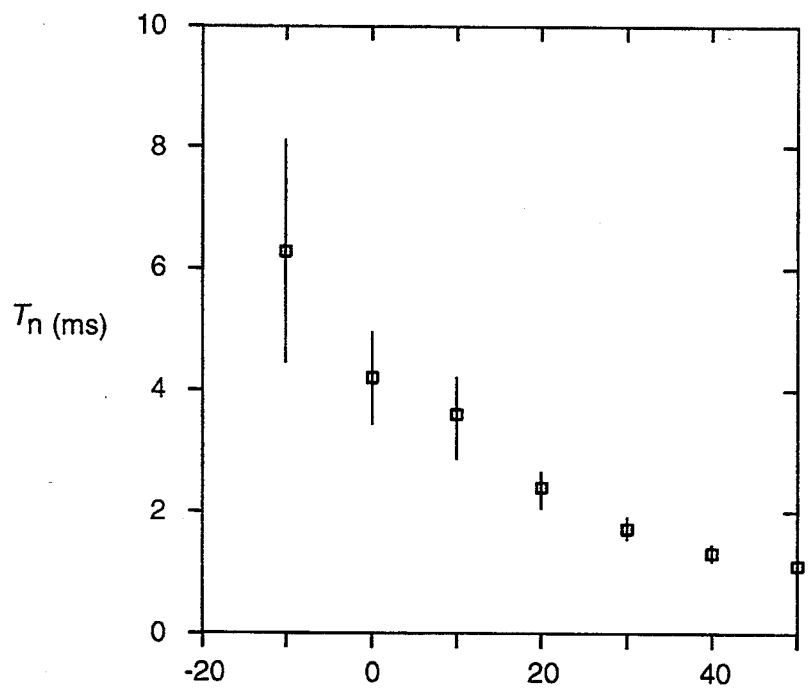
FIG._9

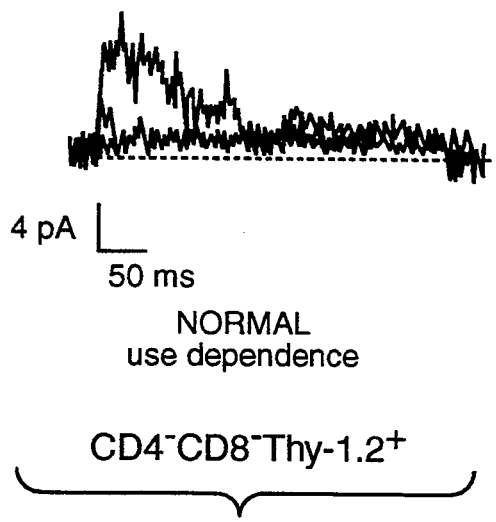
FIG._7A
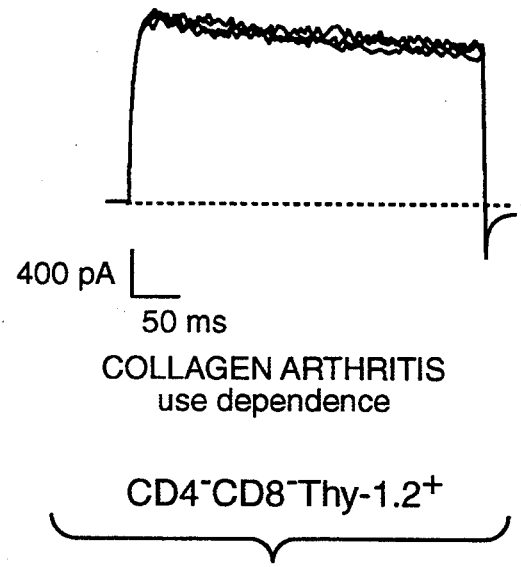
FIG._7B
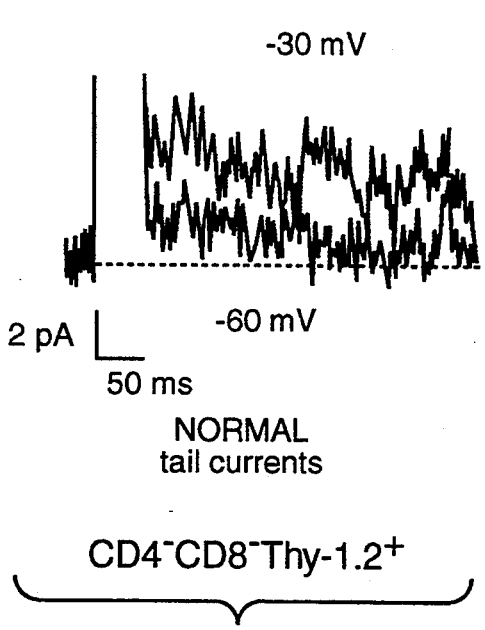
FIG._7C
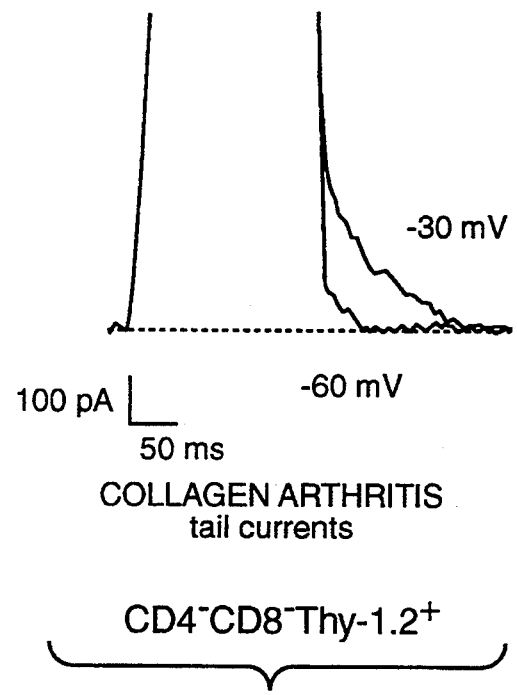
FIG._7D

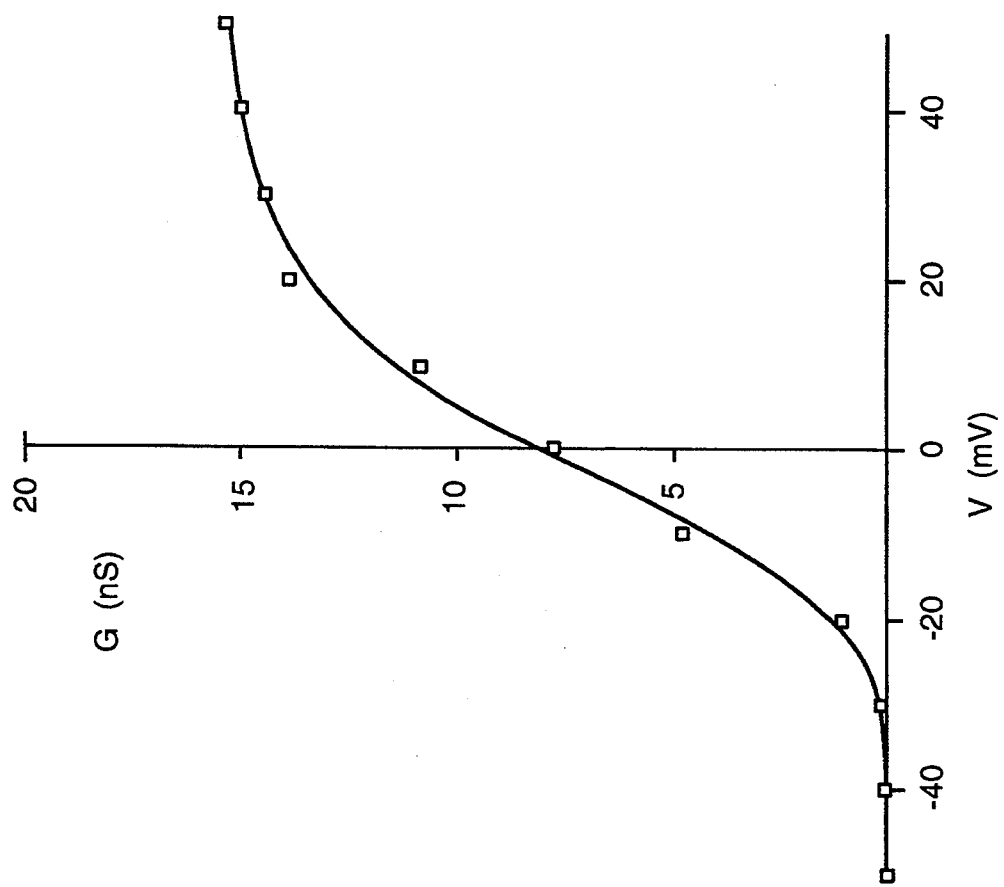
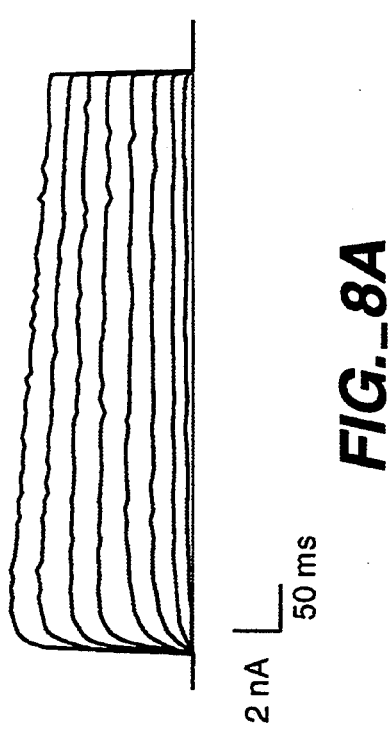
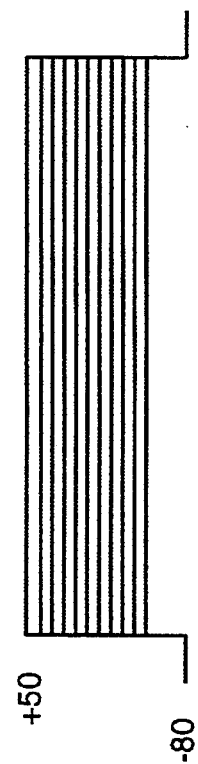

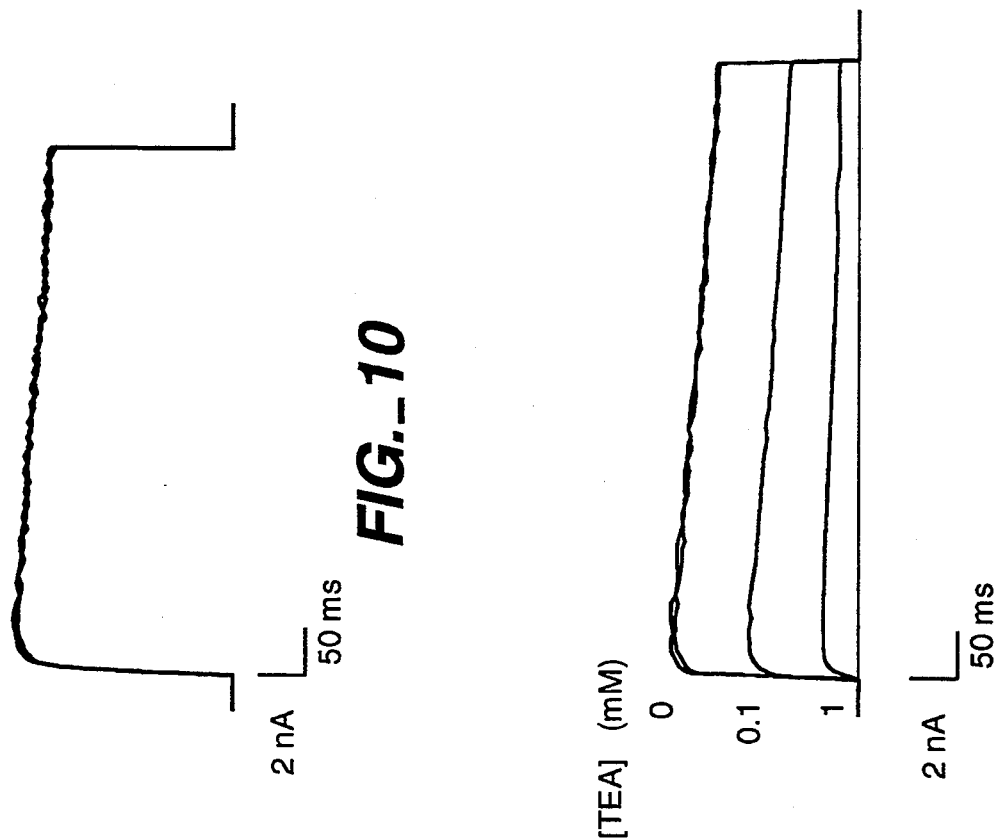

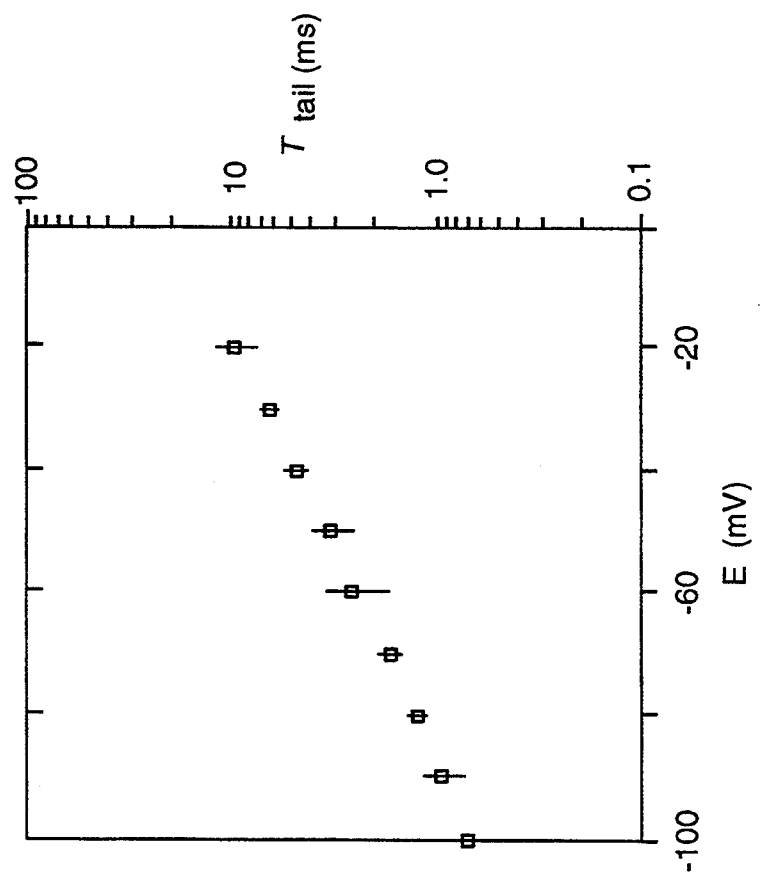
FIG._11C
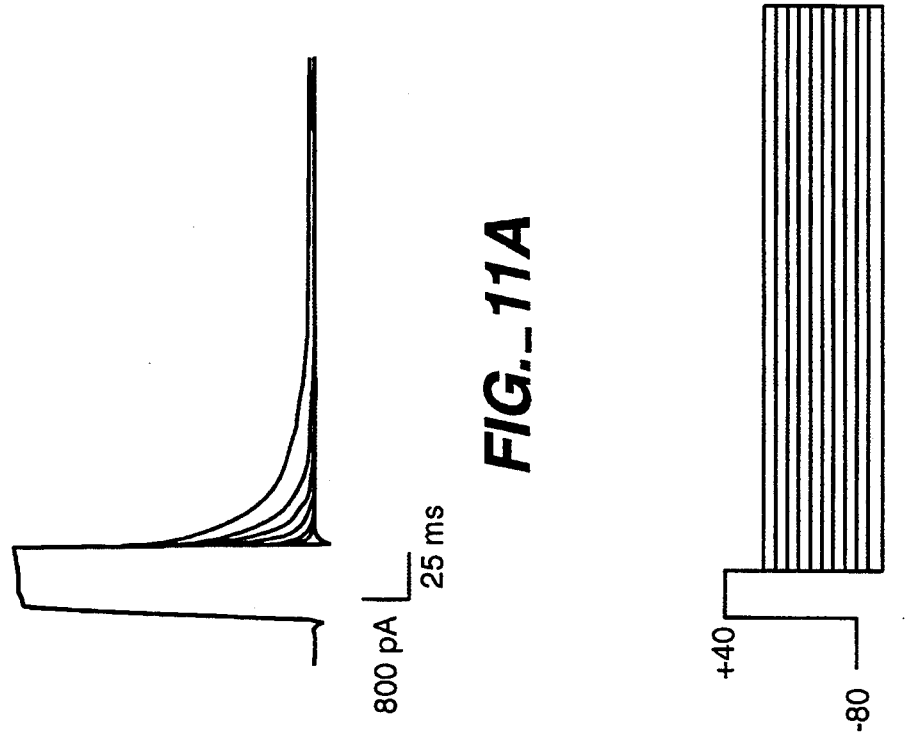
FIG._11A
FIG._11B

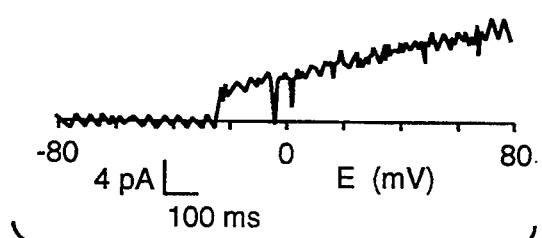
FIG._13A
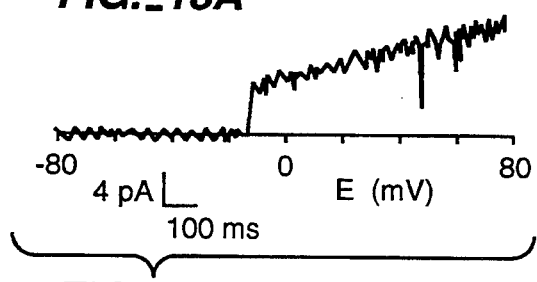
FIG._13B
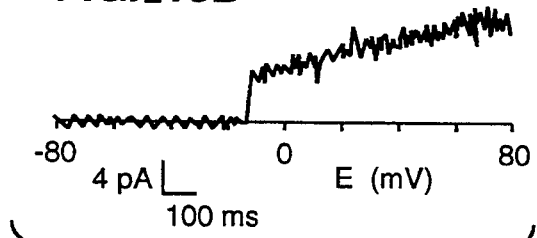
FIG._13C
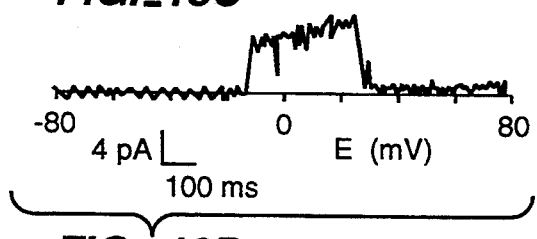
FIG._13D
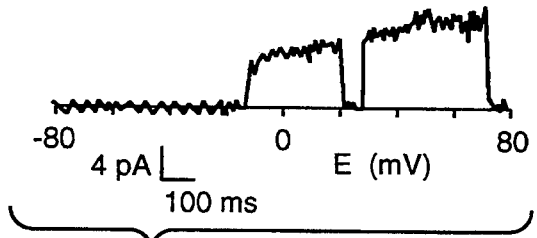
FIG._13E
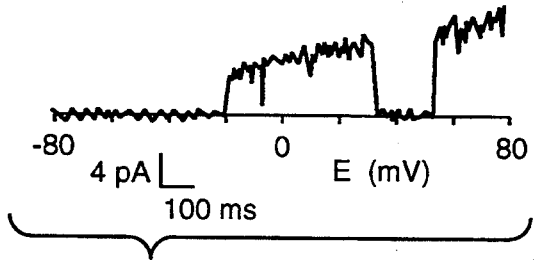
FIG._13F
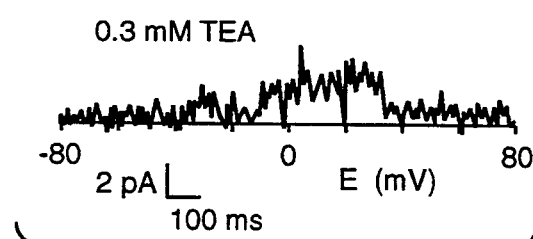
FIG._13G
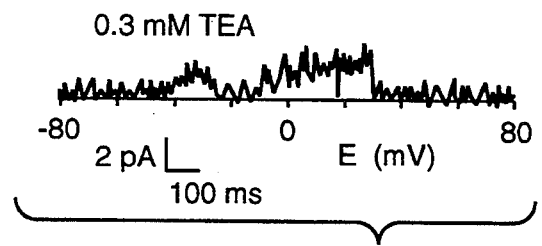
FIG._13H
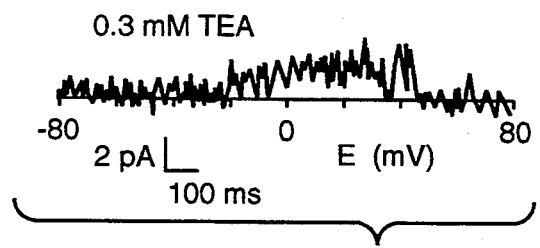
FIG._13I
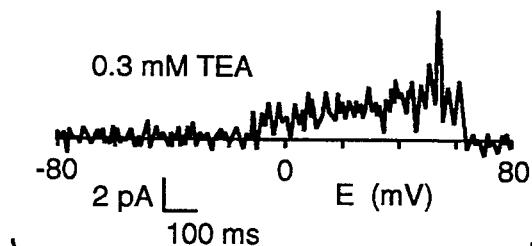
FIG._13J

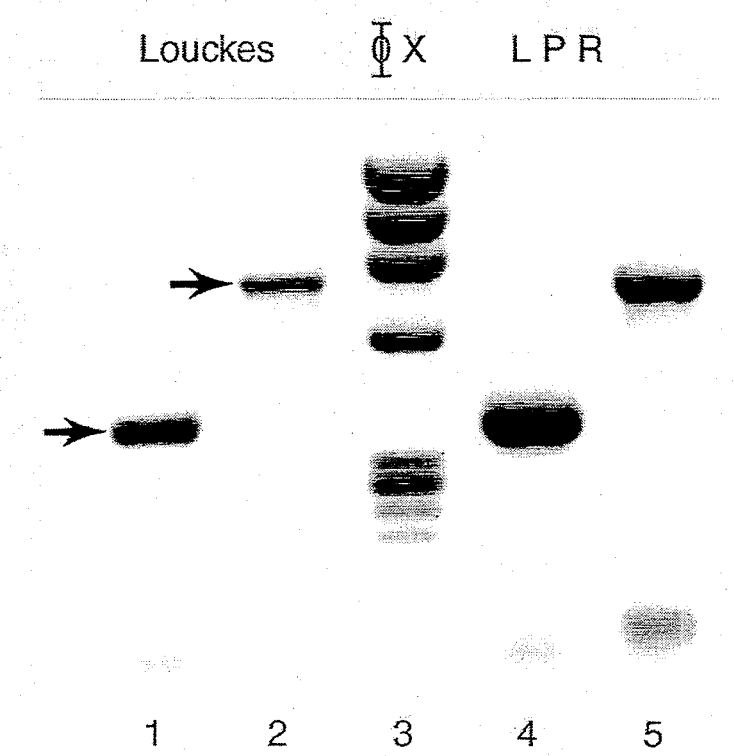
FIG._14

```
CCGCGGTCCT CTGTGCCCCC CGACGGCTGG GGGGAGGGGG GAAGAGGCCC      50

TGCGCCCCCC TCCCCGTCGC CAACTCCCCC TGGCGGCAGC TCCCATGGGT     100

GTCGCTGGGC CGCGCCATGC CTAAGGGGC GCCGCGATGG GCCAAGGGGA      150

CGAGAGCGAG CGCATCGTGA TCAACGTGGG CGGCACGCGC CACCAGACGT     200

ACCGCTCGAC GCTGCGCACG CTGCCCGGCA CGCGGCTTGC CTGGCTGGCA     250

GAGCCGGACG CCCACAGCCA CTTCGACTAT GACCCGCGTG CCGACGAGTT     300

CTTCTTCGAC CGCCACCCGG GCGTCTTCGC TCACATCCTG AACTATTACC     350

GCACCGGCAA GCTTCACTGC CCGGCCGACG TGTGCGGGCC GCTCTACGAG     400

GAGGAGCTGG CCTTCTGGGG CATCGACGAG ACGGACGTGG AGCCCTGCTG     450

CTGGATGACC TATCGCCAGC ACCGAGACGC TGAGGAGGCG CTGGACAGCT     500

TTGGCGGTGC GCCCTTGGAC AACAGCGCCG ACGACGCGGA CGCCGACGGC     550

CCCGGCGACT CGGGCGACGG CGAGGACGAG CTGGAGATGA CCAAGAGATT     600

GGCACTCAGT GACTCCCCAG ATGGCCGGCC TGGCGGCTTC TGGCGCCGCT     650

GGCAACCGCG CATCTGGGCG CTGTTCGAGG ACCCCTACTC ATCCCGCTAC     700

GCGCGGTATG TGGCCTTTGC CTCCCTCTTC TTCATCCTGG TCTCCATCAC     750

AACCTTCTGT CTGGAGACTC ACGAGCGCTT CAACCCCATC GTGAACAAGA     800

CCGAAATCGA GAACGTTCGA AACGGCACCC AAGTGCGGTA CTACCGGGAA     850

GCAGAGACGG AGGCCTTCCT CACCTACATC GAGGGCGTCT GCGTGGTCTG     900
```

FIG.\_15A

```
GTTCACCTTC GAGTTCCTCA TGCGTGTCGT CTTCTGCCCC AACAAGGTGG      950

AATTCATCAA GAACTCCCTC AATATCATTG ACTTTGTGGC CATTCTCCCC     1000

TTCTACCTGG AGGTGGGCCT AAGCGGCCTG TCCTCAAAAG CCGCCAAGGA     1050

CGTTCTGGGC TTCCTGCGCG TCGTCCGCTT CGTGCGCATC CTGCGCATCT     1100

TCAAGCTGAC CCGCCACTTC GTGGGCCTGA GGGTCCTGGG CCACACGCTC     1150

CGTGCCAGCA CCAACGAGTT CCTGCTGCTT ATCATCTTCC TGGCCCTGGG     1200

AGTGCTCATC TTTGCCACCA TGATCTACTA CGCCGAGAGG ATAGGGGCAC     1250

AGCCCAATGA CCCCAGCGCC AGCGAACACA CACACTTTAA AAACATCCCC     1300

ATCGGCTTCT GGTGGGCTGT GGTCACCATG ACGACACTGG GCTATGGAGA     1350

CATGTATCCC CAGACGTGGT CTGGAATGCT GGTGGGAGCC TTGTGTGCTC     1400

TGGCTGGTGT GCTGACCATT GCCATGCCGG TGCCTGTCAT CGTGAACAAT     1450

TTTGGGATGT ACTACTCTTT AGCCATGGCT AAGCAGAAAC TACCAAAGAA     1500

AAAAAAGAAG CATATTCCGC GGCCACCACA GCTGGGATCT CCCAATTATT     1550

GTAAATCTGT CGTAAACTCT CCACACCACA GTACTCAGAG TGACACATGC     1600

CCGCTGGCCC AGGAAGAAAT TTTAGAAATT AACAGAGCAG GTAGGAAACC     1650

TCTCAGAGGC ATGTCGATCT GACCTTTCAC CTCCGCCCCC TGTAGCAATG     1700

ATTCCAGATC CAGTCAGACT GCTTCCTTAG TTCCACGGGC GACCCAGGAT     1750

CCTGTGCCCA ACTTTGAGTT GTGGAGCCTG GGACCCCAGG GAGATGCTGG     1800

GCGGC                                                     1850
```

FIG._15B

```
TTCCTTACCT ACATCGAGGG CGTCTGTGTG GTCTGGTTCA CCTTCGAGTT        50

CCTCATGCGT GTCATCTTCT GCCCCAACAA GGTAGAGTTC ATCAAGAACT       100

CGCTCAACAT CATTGACTTT GTGGCCATCC TGCCCTTCTA CCTGGAGGTG       150

GGGCTGAGCG GCCTGTCCTC CAAGGCAGCC AAGGACGTGC TGGGCTTCCT       200

GCGCGTCGTC CGCTTCGTGC GCATCTTGCG CATCTTTAAG CTGACCCGCC       250

ACTTTGTGGG CCTGCGGGTC CTGGGCCACA CGCTCCGAGC CAGCACCAAC       300

GAGTTCCTGC TGCTCATCAT CTTCCTGGCC TTGGGCGTGC TGATCTTCGC       350

CACCATGATC TACTACGCCG AGAGGATAGG GGCACAGCCC AATGACCCCA       400

GCGCCAGTGA GCACACGCAC TTTAAGAACA TCCCCATCGG CTTCTGGTGG       450

GCCGTGGTCA CCATGACGAC CCTGGGCTAT GGAGACATGT ACCCGCAGAC       500

GTGGTCCGGC ATGCTGGTGG GGGCTCTGTG TGCGCTGGCG GGCGTGCTCA       550

CCATCGCCAT GCCCGTGCCC GTCATCGTGA ACAATTTCGG GATGTATTAC       600

TCCTTAGCCA TGGCTAAGCA GAAACTACCA AAGAAAAAAA AGAAGCATAT       650

TCCGCGGCCA CCGCAGCTGG GATCTCCCAA TTATTGTAAA TCTGTC          696
```

FIG._16

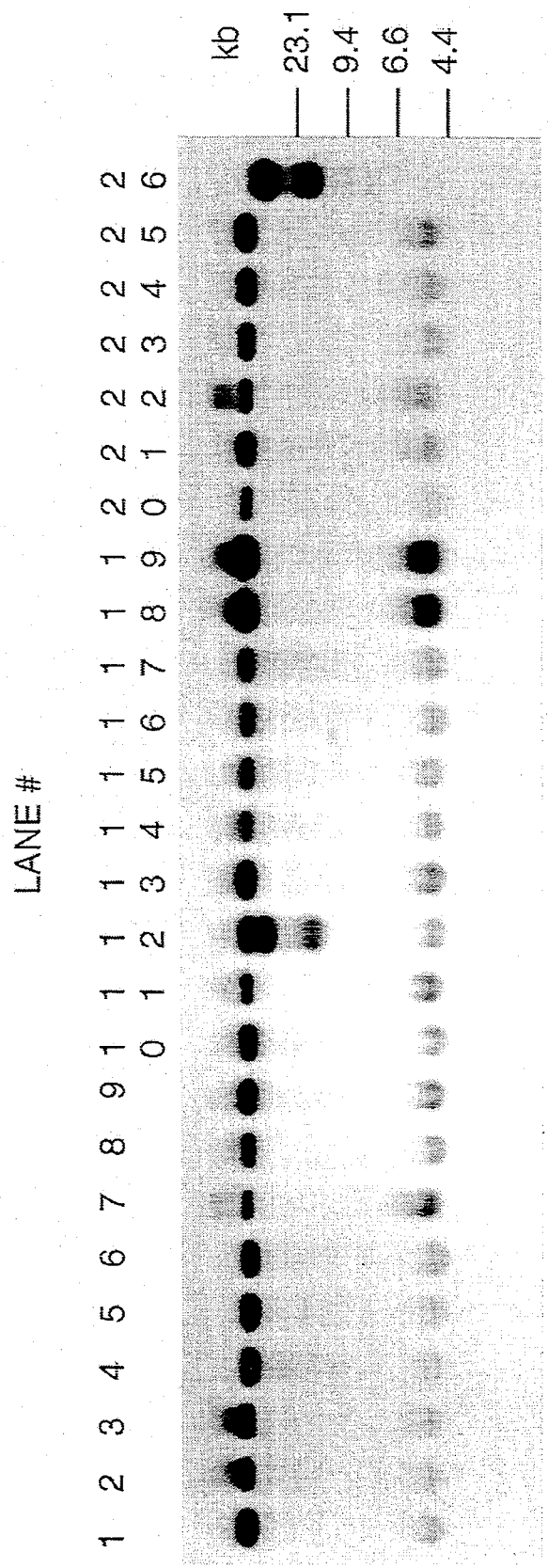
FIG._17

ASSAY FOR AND TREATMENT OF AUTOIMMUNE DISEASES

ACKNOWLEDGEMENT

This invention was made with U.S. Government support in the form of a grant from the National Institutes of Health. The Government has certain rights in this invention.

This application is a continuation-in-part application under 35 U.S.C. 120/121 of application Ser. No. 07/668,609, filed Mar. 13, 1991, which is a continuation-in-part application of application Ser. No. 07/319,499, filed Mar. 6, 1989, abandoned.

FIELD OF THE INVENTION

The present invention relates generally to advances made in the field of autoimmune disease prognosis, diagnosis and treatment. More particularly, the present invention is directed to certain assays for, and consequent treatment of, autoimmune diseases based upon the identification and characterization herein of a unique ion channel aberration found to be associated with abnormal double-negative T cells linked to such diseases. Assays, prognostic markers and therapeutic modalities for such autoimmune disease states are defined and described.

BACKGROUND OF THE INVENTION

Autoimmune diseases have been the subject of widespread press attention because of the considerable morbidity worldwide that they cause. Autoimmune diseases include rheumatoid arthritis, type-1 diabetes mellitus (insulin dependent), multiple sclerosis, myasthenia gravis, systemic lupus erythematosus, Sjogren's syndrome, mixed connective tissue disease, experimental allergic encephalomyelitis (EAE), to name a few. Considerable research has been expended and is currently underway in order not only to devise a treatment or prophylaxis against such devastating diseases, but also to study the underlying etiology(ies) such that a better understanding can be gained as to common denominators, if any, that would more directly focus a plan of attack for conquering them.

In most cases, it is believed that autoimmune diseases result from abnormal cells of the immune system destroying target tissues, either by direct killing or by producing autoantibodies. One may focus for exemplification on historic autoimmune diseases. One such is the so-called systemic lupus erythematosus (SLE). In SLE, abnormal B-lymphocytes produce anti-DNA antibodies that are positively charged and aggregate on negatively charged kidney cells causing inflammation and nephritis, which is symptomatic of SLE. In diabetes mellitus, abnormal T cells systematically destroy pancreatic islet cells such that they prove incapable of producing insulin, a necessary hormone for proper metabolic balance in an organism. In multiple sclerosis, abnormal T cells are believed to damage myelin basic protein, a major component of nerve cells, which systematically destroys certain nerve cells, causing a spectrum of neurological symptoms. In the autoimmune diseases studied to date, there seems to emerge a common pattern of abnormal immune system cells producing materials that either destroy or retard certain target tissues causing symptoms manifest for that disease state.

Current treatment for these diseases remains on an empirical level and is based on causing generalized immunosuppression, either with steroids or other immunosuppressive drugs. This therapeutic approach is also fraught with other problems including associated severe side effects. Further, they serve only to retard the natural progression of these autoimmune diseases. Effective therapeutic treatment, to say nothing of a cure, is beyond present day medical technology. The aberrations in the immune system resulting in these various autoimmune diseases are not well understood, despite the extensive research that has taken place in this field. See Theofilopoulos, et al., *Adv. Immunol.* 37, 269 (1985), for example.

Research has focused on the use of various murine models that have provided considerable insight into the pathogenesis of the disease states, although the clinical syndromes and immunological abnormalities vary considerably from strain to strain, making them less than perfect studies. Thus, a common underlying cellular or molecular defect that is common to all these diseases has not been identified, if indeed there is even a suggestion in the extant art that one exists.

Studies by several investigators have demonstrated that injection of antibodies against $CD_4^+$ $CD_8^-$ T cells prevents, and in some cases retards, the onset of certain autoimmune diseases in certain murine models. See Theofilopoulos, et al., *Adv. Immunol.* 37, 269 (1985); Wofsy, et al., *J. Exp. Med.* 161, 378 (1985); Wofsy, et al., *J. Immunol.* 136, 4554 (1986); Wofsy, et al., *J. Immunol.* 134 852 (1985); Santoro, et al., *J. Exp. Med.* 167, 1713 (1988); Waldor, et al., *Science* 227,415 (1985); Ranges, et al., *J. Exp. Med.* 162, 1105 (1985); Christadoss, et al., *J. Immunol.* 136, 2437 (1986); and Sriram, et al., *J. Immunol.* 136, 4464 (1986). This treatment also results in the reduction of a subpopulation of $CD_4^-$ $CD_8^-$ T cells. In cumulative effect, these data may point to a common underlying mechanism mediated by $CD_4^+$ $CD_8^-$ T cells and/or $CD_4^-$ $CD_8^-$ T cells. See Santoro, et al., *J. Exp. Med.* 167, 1713 (1988).

Existing evidence may further suggest reasons attending the role $CD_4^-$ $CD_8^-$ T cells play in the induction of SLE, for example. First, these cells from diseased SLE mice induce B cells to secrete pathogenic anti-DNA autoantibodies in vitro, whereas the same cells from normal mice or from pre-autoimmune mice do not exhibit this property. Datta, et al., *J. Exp. Med.* 165, 1252 (1987); Sainis, et al., *J. Immunol.* 140, 2215 (1988). Second, the onset of SLE is greatly accelerated in mice that have a severe lymphoproliferation of such cells due to the expression of the autosomal recessive mutations lpr or gld. See Theofilopoulos, et al., supra. Third, patients with SLE nephritis have an expanded $CD_4^-$ $CD_8^-$ T cells population in their blood that induces secretion of autoantibodies. Shivakumar, et al., *FASEB J.* 3, A492 (No. 1548) (February, 1989) and Datta, Federation of American Societies for Experimental Biology Summer Conference on Autoimmunity at Saxton's River, Vt., Jul. 3-8, 1988. Cumulatively, these data may suggest that $CD_4^-$ $CD_8^-$ T cells mediate in some fashion autoimmune disease, contributing to the development of the disease. However, thus far, no marker or alteration or aberration that is unique to the abnormal $CD_4^-$ $CD_8^-$ T cells related to autoimmunity, has been identified.

It was previously reported that $K^+$ channel expression in proliferating $CD_4^- CD_8^-$ T cells from mice with lpr mutations was dramatically altered. Chandy, et al., *Science* 233, 1197 (1986). That research resulted in the association of an abnormal pattern of ion channel expression with an SLE prone genetic defect in cells of the immune system, associated with abnormal lymphoproliferation.

The next step was to determine whether the same abnormal expression pattern could be observed for cells from mice that were not genetically predisposed to SLE, as were the murine models of Chandy, et al., supra. Thus, in Grissmer, et al., *Journal of Immunology* 141, 1137 (1988), murine models that were not prone for SLE, developed similar abnormal expression patterns associated with the onset of SLE and lymphoproliferation. Thus, while in Chandy, et al., supra., abnormal overexpression of type 1 K+ channels in SLE prone murine models was thought to be a lpr mutation dependent abnormality of the immune system, in Grissmer, et al., Supra, similar proliferation of type 1 K+ channels in mice with two distinct mutations (lpr and gld) indicated either that such overexpression was somehow associated with SLE itself or to simple lymphoproliferation symptoms. See also Lewis, et al., *Science* 239, 771 (1988) and DeCoursey, et al., *Nature* 307,465 (1984).

Theofilopoulos, et al., in *Advances in Immunology* 37, 269 (1985), a review article, suggest that the disease profile in the lpr and gld murine models does not resemble any known variant of human SLE. Theofilopoulos, et al. suggest that a clear correlative model is necessary.

Thus, missing in the art is information necessary to establish unequivocally whether, and if so how, abnormal immune cell proliferation and ion channel expression is related etiologically to autoimmune diseases.

Present attention focused on the ion channels themselves. Three types of ion channel types, classified pharmacologically and electrophysiologically, were identified, the so-called n, n' and l types. T cells in the peripheral lymphoid tissues for present purposes, are characterized into relevant types: $CD_4^+CD_8^-$, $CD_4^-CD_8^+$, $CD_4^-CD_8^-$. The $CD_4^+CD_8^-$ cells are thought to express approximately 20 n channels per cell and are believed to have no n' and l channels. $CD_4^-CD_8^++T$ cells are thought to have about 20 n' and l channels per cell and no n channels. And $CD_4^-CD_8^-$ T cells are believed to express about 20 channels per cell, all three types being represented. In a normal immune response reflecting induction of activity, such as with mitogens, the n channel types are increased upwards of ten-fold in the cells that are activated. Thus, normal T cells when stimulated by mitogens, show as a normal immune response elevation in the number of n channels. Blocking these n channels, for example with tetraethyl ammonium (TEA), would serve to shut down and effectively block an immune response. Abnormal T cells may also be subject to a similar blockage. However, such abnormal T cells are represented by $CD_4^-CD_8^-$ cells, manifesting a proliferation of type 1 channels. Type 1 K+ channels are not use dependent, close more rapidly on repolarization than do n channels and are much more sensitive to blockage, for example by TEA. It was the unsuggested goal of the present research to establish a link, if any, hence an etiology, between abnormal ion channel expression in immune cells and systemic symptoms of autoimmune disease states. A further goal of the present research was to isolate and characterize the nucleic acid sequences which encode the type 1 K+ channel.

SUMMARY OF THE INVENTION

The threshold experiment establishing the aforementioned link was performed with murine models that are representative of human SLE, namely, NZBxNZW, NZBxSWR, BXSB-Yaa and MRL-+/+. In these models, it was found herein that in the case of SLE, as one example of an autoimmune disease, the unique pattern of type I K+channel expression in $CD_4^-CD_8^-$ T cells was associated with the onset of SLE, rather than it being a result of abnormal lymphoproliferation. Thus, the link was established, eliminating the possibility that what was being observed in earlier studies was simply symptomatic of the lymphoproliferative autoimmune disease.

The present invention is predicated upon the identification and characterization of an etiology of autoimmune diseases, represented by SLE, type-1 diabetes mellitus, experimental allergic encephalomyelitis (EAE), and others, namely, that all such autoimmune diseases demonstrate uniquely the presence of abnormal $CD_4^-CD_8^-$ T cells expressing large numbers of type 1 K+ ion channels. Thus, such channel expression parallels the ability to induce autoimmunity. Having established such a link as a predicate of the present invention, it intellectually follows that the present invention is directed to several consequential aspects:

1) an assay for determining presence of an autoimmune disease state by measuring the relative numbers of type 1 K+ channels in abnormal $CD_4^-CD_8^-$ T cells by using electrophysiological or nucleic acid-based assays, 2) an assay for screening and identifying extrinsic materials for their ability to selectively modulate type 1 K+ channels in abnormal $CD_4^-CD_8^-$ T cells, 3) selected identified extrinsic materials and their use as principles in drug regimens to treat systemically the target autoimmune disease, 4) a method of treating an individual suffering from an autoimmune disease state using such principles, and 5) associated test kits and other embodiments germane to these aspects.

Thus, the present invention is predicated upon the identification and characterization of a diagnostic marker for autoimmune diseases, that leads to a general diagnostic and a therapeutic target for such diseases. This predicate makes possible the identification of the etiology of a given autoimmune disease state, an assay to detect presence of the marker, an assay to identify (selective) modulators of the marker, suitable modulators identified from such an assay and therapeutic modalities based upon such modulators (drugs) and/or specific antibodies raised against type 1 K+ channels of abnormal $CD_4^-CD_8^-$ T cells.

Thus, the quintessence of the present invention enables in turn the consequence that the identified elevated numbers of type 1 K+ channels in abnormal $CD_4^-CD_8^-$ T cells can be exploited by a method of screening for extrinsic materials having a modulating effect on such channels comprising providing an in vitro system containing elevated type 1 K+ channels of abnormal $CD_4^-CD_8^-$ T cells, challenging such cells with one or more of a battery of test materials having the putative potential to modulate said type 1 K+ channels, monitoring the effect of said test materials on said type 1 K+ channels and selecting candidates capable of modulating type 1 K+ channels.

The present invention is also directed to a method for diagnosing generally for presence of an autoimmune disease state comprising providing T cells containing $K^+$ channels from a test individual, identifying abnormal T cells from among the population of the provided T cells, measuring the relative numbers of type 1 $K^+$ channels of the abnormal cells, and determining whether said type 1 $K^+$ channels are elevated over normal.

The present invention is additionally directed to a method for treating autoimmune diseases that are symptomatized by elevated numbers of type 1 $K^+$ channels in abnormal $CD_4^-CD_8^-$ T cells of the immune system of the organism manifesting said autoimmune disease which comprises contacting said organism and/or said immune cell system with an extrinsic material having a modulating effect on said type 1 $K^+$ channels, such materials optionally identified via the assay system described supra. In particular, the present invention is directed to a method of treating autoimmune diseases as described above, selectively without disturbing type n and n' ion channels expression characteristic of normal immune response comprising treating an organism or cells as described above with, as an example, tetraethyl ammonium (TEA) or such other selective modulator defined and optionally selected via the assay described supra.

The present invention is further directed to kits containing associated structure, reagents and means to conduct diagnostic or screening assays as described supra.

Further, the present invention is directed to the foregoing aspects in all of their associated embodiments as will be represented as equivalents within the skill of those in the art.

The present invention is thus directed to the identification, management and control of autoimmune diseases, including:

(1) use as a prognostic tool, for example, by making reactive antibodies to the type 1 $K^+$ channels and measuring the numbers thereof or through the use of nucleic acid-based screening methods, and/or (2) selectively screening for, preferably selective, modulators of type 1 $K^+$ channels for use as a diagnostic, and/or (3) blocking, retarding or eliminating selectively type 1 $K^+$ channels for use as a therapeutic.

In respect of the above, it is contemplated that one could link a reactive antibody with a cell toxin such that the antibody would locate and bind to a type 1 $K^+$ channel of an aberrant $CD_4^-CD_8^-$ T cell (contributing to an autoimmune disease) and thereby place the cell toxin, e.g., ricin, in close proximity to the target abnormal cell with consequential predetermined cytotoxic activity. One could use Psoralen to image the aberrant target cells followed by activation to a cytotoxin, as above.

Also, the present invention is directed towards the use of nucleic acid sequences encoding the type 1 $K^+$ channel to screen populations of T cells isolated from individuals in order to detect the presence of an autoimmune disease by detection of increased levels of type 1 channel mRNA.

The present invention is illustrated herein by use of murine models representative of human etiology. Evidence for this lies in the fact that (1) $CD_4^-CD_8^-$ cell types induce, in all systems studied, abnormal autoimmune disease causing cells, (2) these $CD_4^-CD_8^-$ T cells possess, in all models studied, abundant numbers of type 1 $K^+$ channels, and (3) type 1 $K^+$ channels are known to exist in humans. See Shapiro, et al., *Biophysical Journal* 53,550a, No. W-Pos203 (1988). By virtue of the present invention using such murine models, there has been found an established link to autoimmune diseases of elevated type 1 $K^+$ channels in abnormal T cells; therefore, the present invention is translatable to immune systems having $CD_4^-CD_8^-$ T cells bearing type 1 $K^+$ channels, for example, as found in humans.

DETAILED DESCRIPTION OF THE INVENTION

The present invention is illustrated using characteristic murine models that establish, with proper correlation and translation into the human system, that type 1 $K^+$ channels are elevated in abnormal $CD_4^-CD_8^-$ T cells on onset of a given autoimmune disease. Illustrative autoimmune diseases tested were SLE, type-1 diabetes, type II collagen rheumatoid arthritis (a model for rheumatoid arthritis), and EAE (a model for multiple sclerosis), all with characteristic murine models. Given the results of the model systems employed, and given the instant disclosure of how to assay for and diagnose and treat an autoimmune disease based on such results, one skilled in the art will well enough know how to carry out such endeavors using the human system, when it is possible to proceed in this manner unhampered by government regulatory impediments.

BRIEF DESCRIPTION OF THE DRAWINGS

FIG. 1: $K^+$ channel expression in splenic and LN-derived $CD_4^-CD_8^-$ T cells in normal mice and mice with SLE. (a) Representative whole-cell $K^+$ currents in $CD4^-CD8^-$ T cells in normal mice (left, BALB/c) and mice with SLE (right). Note the different current scales, $K^+$ currents were elicited by 200 ms depolarizing pulses to 30 mV (holding potential $-80$ mV). Two current traces superimposed before and during application of a Ringer solution containing 10 mM (left) or 0.1 mM (right) $TEA^+$, respectively. (b) Maximum $K^+$ conductances ($g_k$) in normal and several strains of mice with lupus. ▲, □, ● represent n, 1, n' $K^+$ channel types. $g_k$ was determined from the maximum peak $K^+$ current elicited at $+40$ MV, assuming a reversal potential for $K^+$ of $-80$ mV. Each point represents $g_k$ in one single cell. Data from C3H (n=12), C3H-lpr (n=22), C3H-gld (n=26), and MRL-lpr (n=31) are included in the graph for comparison. These data are shown as mean ±SD. Dividing $g_k$ by the single channel conductance gives an estimate of the numbers of channels to each. Average $g_k$(mean±SEM) of $CD4^-CD8^-$ T cells, normal mice, 405±53 pS, n=SE SLE mice, 4550±254 pS, n=76; lprgld mice, 4935±325 pS, n=79. $CD_4^-CD_8^-$ T cells from normal mice exhibit one or more of n, n' or 1 channels at above 20 per cell In contrast, $CD_4^-CD_8^-$ T cells from lupus mice have ~200 channels per cell that are primarily type 1.

FIG. 2: $K^+$ channel expression in splenic and lymph node $CD_4^-CD_8^-$ Thy-1.2$^+$ T cells in young healthy and old diseased SLE mice.

FIG. 3: $K^+$ channel expression in $CD4^-CD8^-$ cells in normal mice, and in mice with type-1 diabetes mellitus (NOD) and mice with chronic EAE (a model for multiple sclerosis). NOD and EAE: each data point represents $g_k$ in one single cell; normal mice, mean±SD of cells shown in FIG. 3. ▲, □, ● represent n, 1, n' $K^+$ channel types. Average $g_k$ (mean±SEM) of $CD4^-CD8^-$ T cells; NOD mice, 5795±1253 pS, n=21; chronic EAE ($g_k$ >1000 pS), 6083±1277 pS, n=10; chronic EAE ($g_k$ <1000 pS), 396±84 pS, n=1). $CD_4^-CD_8^-$ T cells from mice with either NOD or chronic EAE exhibit large numbers of type 1 K+ channels whereas normal $CD_4^-CD_8^-$ T cells exhibit small numbers of n, n' or l channels.

FIG. 4: A, Maximal K+ conductance ($g_k$) Of $CD_4^-CD_8^-$ Thy-1.2+ T cells in normal mice and mice with type II collagen arthritis: ▲, □, ● represent n, 1, n' K+ channel types. These data are shown as mean±SD. B, Percentage of cells with $g_k$>1000 pS of type 1 K+ conductance. Data for normal mice are pooled together from C3H, C57BL, BALB/c, and DBA/1-LACJ (uninjected).

FIG. 5: Maximal K+ conductance ($g_k$) of helper T cells $CD_4^+CD_8^-$ and killer T cells $CD_4^-CD_8^+$ subsets in normal mice and mice with collagen arthritis. ▲, □, ● represent n, 1, n' K+ channel types Thus, helper and killer T cell subsets in diseased mice maintain their channel phenotype like normal helper and killer T cells.

FIG. 6: Maximal K+ conductance ($g_k$) of $CD_4^-CD_8^-$ Thy-1.2+ T cells in uninjected DBA/1-LACJ mice, BALC/c mice injected with heat-killed E. coli, and DBA/1-LACJ mice injected with CFA at day −26, −62 and −26, −26 and −2. Day 0 refers to the day the electrophysiological experiments were performed. ▲, □, ● represent n, 1, n' K+ channel types.

FIG. 7: Whole cell K+ currents in CD4−CD8− Thy-1.2+ T cells in normal mice (left) and mice with collagen arthritis (right). Top, K+ currents were elicited with 200 ms depolarizing pulses to 40 mV from a holding potential of −80 mV. Pulse interval was 1 sec to assay cumulative (use-dependent) inactivation. Note the different current scale. Bottom, tail currents were elicited by voltage steps to −60 and −30 mV after a 15 ms prepulse to 40 mV. Note the different current and time scale.

FIG. 8: K+ currents in an outside-out patch from an oocyte injected with mKv3.1b mRNA. The membrane potential was −80 mV, and depolarizing pulses were applied every 30 s. The test potential was changed from −50 to 50 mV in 10 mV increments. B) Peak K+ conductance-voltage relation for the K+ currents are shown in A. The line through the points was fitted with the Boltzmann equation:

$$gK(E) = \overline{gK}\text{max}/\{1+\exp[(E_n-E)/k]\}$$

with parameter values: $\overline{gK}$ max=16.1 nS; $E_n$=0 mV; k=−15.6 mV.

FIG. 9: Activation time constants, $\tau_n$, were obtained by fitting curves through the current data points of traces similar to those shown in FIG. 8 according to a Hodgkin-Huxley type $n^4h$ model:

$$I_{total} = I_K \text{max}[1-\exp(-t/\tau_n)]^4 \exp(-t/\tau_h)$$

The points represent averages of $\tau_n$ obtained from five different patches; the bars indicate the SEM.

FIG. 10: Cumulative (use-dependent) inactivation of mKv3.1b K+ currents in an outside-out patch from an oocyte injected with mKv3.1b mRNA. Currents were elicited by a train of 6 depolarizing voltage steps to +40 mV once every second from a holding potential of −80 mV. The test pulse duration was 200 ms. The K+ current amplitude did not decrease during this train.

FIG. 11. Kinetics of deactivation of mKv3.1b K+ currents in an outside-out patch from an oocyte injected with Kv3.1 mRNA. Tail currents were elicited by voltage steps from −100 to −20 mV after a 15 ms depolarizing prepulse to +40 mV. Tail current-decay time constants, $\tau_{tail}$ were fitted with single exponentials and plotted vs. the applied membrane potential, E, during the decay (right). The squares represent $\tau_{tail}$ for Kv3.1 in 5 patches; the bars indicate the SEM.

FIG. 12: Pharmacology of the mKv3.1b K+ channels. Effect of 0.1, 1, and 20 mM TEA on mKv3.1b K+ currents in an outside-out patch from an oocyte injected with mKv3.1b mRNA (left). K+ currents were elicited with depolarizing pulses to +40 mV from a holding potential of −80 mV every 30 s before and during treatment with various TEA concentrations. Dose response curve for TEA block of mKv3.1b K+ current (right). The line through the points was fitted by eye, yielding a Kd for TEA of 0.15 mM.

FIG. 13: Single-channel currents of mKv3.1b K+ currents in normal Ringer solution (left) and in the presence of 0.3 mM TEA (right) measured in an outside-out patch from an oocyte injected with mKv3.1b mRNA. The holding potential was −80 mV and the membrane potential was continuously ramped from −80 mV to +80 mV within 450 ms every second. Single-channel events can be seen at potentials positive to −10 mV. Fitting a line through the slope of the current during openings gives an estimate of 27 pS for the single-channel conductance in Ringer; the line intercepts the voltage axis near −80 mV, close to the equilibrium potential for K+. In the presence of TEA, the single-channel conductance is 9 pS.

FIG. 14: Kv3.1 is expressed in MRL-lpr mouse T cells and human Louckes cells. PCR amplification of 774 bp and 390 bp fragments from Louckes cDNA (left two lanes) and from MRL-lpr lymph node cDNA (right two lanes) with Kv3.1-specific primers. The middle lane shows the phi-X molecular weight markers from top to bottom (in bp): 1353, 1078, 872, 603, 310, 281, 271, 234, 194, 118, and 72.

FIG. 15: Nucleotide sequence of the mouse Kv3.1b transcript (SEQ ID NO: 6).

FIG. 16: Nucleotide sequence of the partial human Kv3.1 transcript (SEQ ID NO: 5).

FIG. 17. Southern blot showing hybridization of the 1.7 kb Kv3.1 probe to the somatic cell hybrid mapping panel. All DNAs are digested with EcoRI. Lane 1 is genomic DNA from the hamster parental cell line (UCW56). Lane 26 is total human genomic DNA. Human-specific hybridization is evident to DNA from the human/hamster hybrid in lane 12 (HHW1049). HHW1049 contains human chromosomes 5 and 11. This is the only hybrid on the panel that contains a human chromosome 11. All other human chromosomes are represented including 18 hybrids with either intact or derivative human chromosomes 5. Kv3.1 therefore maps to human chromosome 11. A complete table indicating the human content of all the hybrids in this panel can be found elsewhere (Liptay et al., Genomics 13, 287 (1992)).

DEFINITIONS

By the term "extrinsic material" herein is meant any entity that is not ordinarily present or functional with respect to type 1 K+ channels and/or abnormal $CD_4^-CD_8^-$ T cells and that affects same. Thus, the term has a functional definition and includes such identified entities as hormones; toxins; growth factors/cytokines; secondary messenger modulating substances;

organic compounds and inorganic compounds; agents that indirectly impact on the l channel through effects on intracellular second messengers, or other channels, or membrane potential or receptors; cell types targeted to type 1 K+ channels or abnormal $CD_4^-CD_8^-$ T cells; genetic manipulation products impacting on l channels or on $CD_4^-CD_8^-$ T cells; or bacterial or viral materials that impact on $CD_4^-CD_8^-$ T cells having many l channels.

By the term "modulating effect" or "properties", or grammatical equivalents, herein is meant both active and passive impact on type 1 K+ channels and/or abnormal T cells. These include, but shall not be construed as limited to, blocking the channel or the function of the channel protein(s), reducing the number of ion channels per cell and use of secondary cell(s) or channel(s) to impact on a primary abnormal cell.

By the term "monitoring" in respect of effect of test materials on type 1K+ channels and/or abnormal T cells herein is meant any method known or devised for measuring the impact of a test material on said channels/cells. These include, but shall not be construed as limited to, measuring current, measuring membrane potential, measuring K+ flux, such as with radioactive tracers, measuring K+ concentration and measurements of indirect consequences to other receptors, second messengers and/or channels.

The term "autoimmune disease" herein has meaning beyond the classical definition, and therefore, shall include any disease state where $CD_4^-CD_8^-$ T cells act as accessory cells, for example, to induce the immune system to result in destruction of organism cells.

EXAMPLES

The following examples detail materials and methods employed in the experimental procedures that follow:

A gigohm seal patch-clamp technique was employed [Hamill, et al., *Pflugers Arch.* 391, 85 (1981)]. Cells were separated and stained as described infra. Maximum K+ conductances ($g_k$) Of $CD_4^-CD_8^-$ Thy-1.2+T cells were determined from the maximum peak K+ current elicited at +40 mV (holding potential −80 mV), assuming a reversal potential for K+ of −80 mV. All experiments were done at room temperature (22° to 26° C.). The cells under investigation were bathed in Ringer solution (in mM): 160 NaCl, 4.5 KCl, 2 $MgCl_2$, 1 $CaCl_2$, 2 $MgCl_2$, and 10 K-HEPES (pH 7.4). The patch pipette contained 134 KF, 11 $K_2$-EGTA, 1.1 $CaCl_2$, 2 $MgCl_2$, and 10 K-HEPES (pH 7.2). Each point represents $g_k$ in one single cell except the ones with the bars that reflect the mean±SD of previously reported data. The data from C3H (n=12), C3H-lpr (n=22), C3H-gld (n=26), and MRL-lpr (n=31) are taken from Grissmer, et al., *J. Immunol.* 141, 1137 (1988) and Chandy, et al., *Science* 233, 1197 (1986)2, respectively, and are included in the graph for comparison. Three types of voltage-gated K+ channels (n, l, n') are expressed by murine T cells, which can be distinguished by electrophysiological and pharmacological criteria. DeCoursey, et al., *J. Gen. Physiology* 89, 379 (1987).

$g_k$ of $CD_4^-CD_8^-$ T cells from three young MRL-+/+ mice, before the onset of clinically symptomatic disease and two old MRL-+/+ mice with lupus nephritis (proteinuria: >2000 mg protein/dl) was determined as described above in connection with FIG. 1. Each point represents $g_k$ in one single cell except the ones with the bars that reflect the mean±SD of previously reported data (Grissmer, et al., *J. Immunol.* 141, 1137 (1988) and Chandy, et al., *Science* 233, 1197 (1986).) See FIG. 2.

Splenic $CD_4^-CD_8^-$ Thy-1.2+ T cells from mice with clinically evident SLE (MRL-+/+, NZB x SWR, NZB x NAW, BXSB-males) display numerous type 1 K+ channels/cell (FIG. 1) with an average $g_k$ of 4550±254 pS (mean±SEM, n=76). Dividing the $g_k$ by the single channel conductances [Lewis, et al., *Science* 239, 771 (1988)] gives an estimate of 100-200 type 1 K+ channels. Previous data on K+ channel expression in $CD_4^-CD_8^-$ Thy-1.2+ T cells from C3H-lpr ($g_k$: 5223±565 pS; mean±SEM, n=22), C3H-gld ($g_k$: 5092±503 pS; mean±SEM, n=26), MRL-lpr ($g_k$: 4600±600pS; mean±SEM, n=31) mice [Grissmer, et al., *J. Immunol.* 141, 1137 (1988) and Chandy, et al., *Science* 233, 1197 (1986)], is presented for comparison. Occasionally, cells with small numbers of type n K+ channels were observed; these may represent normal cells. In contrast, $CD_4^-CD_8^-$ Thy-1.2+ T cells from the spleen and lymph nodes of normal mice (C57BL, BALB/c), varying in age from 1-19 months, express types n, l or n' K+ channels, with a low average $g_k$ of 458±63 pS (mean±SEM, n=39) representing about 10-20 K+ channels/cell. Thus, $CD_4^-CD_8^-$ Thy-1.2+ T cells from every murine model for SLE, display an abnormally elevated number of type I K+ channels, demonstrating from the (as labeled) Lupus models that the alteration is linked to the disease.

Besides the murine SLE models, the non-obese diabetes (NOD) mouse strain is another genetically determined murine model for autoimmune disease [Makino, et al., *Exp. Anim.* 29, 1 (1980) and Hattori, et al., *Science* 231, 733 (1986)]. These mice spontaneously develop type-1 diabetes mellitus $CD_4^+CD_8^-$ and $CD_4^-CD_8^+$ T cells have been implicated in the pathogenesis of this disease [Miller, et al., *Nature* 307, 465 (1984), O'Neil, et al., *J. Immunol.* 140, 52 (1988) and Koike, et al., *Diabetes* 36, 539 (1987)]. The role of $CD_4^-CD_8^+$ Thy-1.2+ T cells has not been examined. Splenic $CD_4^-CD_8^-$ Thy-1.2+ T cells from NOD mice with clinical evidence of type-1 diabetes mellitus, exhibited large numbers of type 1 K+ channels, with an average $g_k$ of 5795±1253 pS (mean±SEM, n=21), reflecting about 200 type 1 K+ channels/cell. This pattern of K+ channel expression is almost identical to that in $CD_4^-CD_8^-$ Thy-1.2+ T cells from SLE mice, showing a common mechanism underlying type-1 diabetes mellitus and SLE. A relatively larger fraction of the splenic $CD_4^-CD_8^-$ T cells (421) in mice with type-1 diabetes mellitus, displayed lower $g_k$ than observed in SLE mice (4/76). This difference in K+ channel expression in the spleen may reflect the organ-specific nature of the autoimmune manifestations in type-1 diabetes mellitus, which are primarily confined to the pancreas, and the systemic autoimmune manifestations in SLE.

Since murine SLE and type-1 diabetes mellitus are genetically determined diseases, alteration in K+ channel expression may be present from birth. To address this question a comparison of K+ channel expression in $CD_4^-CD_8^-$ Thy-1.2+ T cells from young and old MRL-+/+ mice was undertaken. $CD_4^-CD_8^-$ Thy-1.2+ T cells from young MRL-+/+ mice displayed an order of magnitude fewer K+ channels ($g_k$: 295±91 pS; mean±SEM, n=11; ≈10 channels/cell) compared to older MRL-+/+($g_k$: 5306±518 pS; mean±SEM, n=18; ≈200 channels/cell) with clinical evidence of lupus nephritis (FIG. 2). Earlier data on $CD_4^-CD_8^-$ Thy-1.2+ T cells from young healthy C3H-lpr ($g_k$:

324±67 pS; mean±SEM, n=17; ≈12 channels/cell) mice are presented for comparison. The pattern of $K^+$ channel expression in autoimmune mice, prior to the onset of clinically symptomatic disease, resembles that in $CD_4^- CD_8^-$ Thy-1.2+ T cells from normal mice (compare FIGS. 1 and 2). These data demonstrate that abnormal $K^+$ channel expression in $CD_4^- CD_8^-$ T cells parallels the development of disease and reflects the ability of these cells to induce the secretion of pathogenic anti-DNA autoantibodies.

Experimental allergic encephalomyelitis (EAE) is considered to be a model for human multiple sclerosis. Mice inoculated with myelin basic protein develop paralysis within 1-2 weeks (acute EAE). Some of these mice recover and then develop a chronic relapsing disease (chronic EAE) which closely resembles human multiple sclerosis. $CD_4^- CD_8^-$ Thy1.2+ splenic T cells were isolated from mice with chronic EAE and their $K^+$ channel expression was studied. A greater frequency of cells exhibited large numbers of type l $K^+$ channels compared to normal mice. This pattern of $K^+$ channel expression is similar to that in $CD_4^- CD_8^-$ Thy 1.2+ from mice with SLE and type-1 diabetes mellitus, showing a common mechanism underlying these three distinct autoimmune diseases. A larger fraction of $CD_4^- CD_8^-$ Thy 1.2+ cells had normal numbers of $K^+$ channels/cell compared with mice with SLE. The autoimmune process in chronic EAE is primarily confined to the nervous system and changes in the spleen would not be as evident as in SLE which is primarily a systemic autoimmune disease with a major autoimmune process taking place in the spleen.

Other subsets of T lymphocytes ($CD_4^+ CD_8^-$ or $CD_4^- CD_8^+$) from diseased BXSB-male mice and from C3H-lpr, C3H-gld mice exhibited small numbers of types l, n, or n' $K^+$ channels like phenotypically identical cells from normal mice. Normal mitogen activated T cells express ≈200 type n $K^+$ channels/cell [DeCoursey, et al., *J. Gen. Physiol.* 89, 405 (1987)], in contrast to the numerous type l $K^+$ channels displayed by $CD_4^- CD_8^-$ Thy-1.2+ T cells in mice with SLE and type-1 diabetes mellitus. These data demonstrate that abundant type l $K^+$ channel expression is an unique feature of diseased $CD_4^- CD_8^-$ T cells, and is different from the pattern of $K^+$ channel expression in normal T cells induced by mitogens.

$K^+$ channels were identified on the basis of their inactivation properties, channel closing kinetics, and sensitivity to block by tetraethylammonium (TEA). Typically type n $K^+$ channels are use-dependent, i.e., show cumulative inactivation by repetitive depolarizing pulses. Use dependence was determined by measuring the decline in the size of the peak $K^+$ current elicited with one per second repetitive depolarizing pulses of 200 ms duration. Type n $K^+$ channels also close slowly upon repolarization with a time constant of about 30 ms at −60 mV and are blocked by TEA+ ($K_D$=8 mM). Type l $K^+$ channels are not use dependent, close more rapidly on repolarization with a time constant of 2 ms at −60 mV, and are much more sensitive to block by TEA+ ($K_D$=0.1 mM). Type n' $K^+$ channels are not use dependent, close slowly like type n $K^+$ channels upon repolarization, but are less sensitive to block by TEA+ ($K_D$=100 mM).

For the above experiments, mice were housed in the Vivarium at U.C. Irvine, and care was taken in accordance with institutional guidelines. The mice were lightly anesthetized with metofane, and sacrificed by cervical dislocation. The spleen was removed and single cell suspensions prepared. Cells were washed three times with RPMI-1640 (Irvine Scientific, Santa Ana, Calif.) supplemented with 10% fetal calf serum (Hyclone, Logan, Utah). Cells were resuspended at $10 \times 10^6$ cells/ml and T cells separated from non-T cells by a nylon wool column. The cells were washed three times in medium, and resuspended at $1$–$2 \times 10^6$ cells/ml. The cells were stained as follows: Cells were first incubated on ice for 30 minutes with rat-anti-mouse-CD4 and rat-anti-mouse-CD8 antibodies, washed three times in medium, incubated for 30 minutes on ice with phycoerythrin-conjugated goat-anti-rat-IgG (affinity purified and absorbed for mouse Ig), washed three times in medium, incubated on ice for 30 minutes with fluorosceinated rat-anti-mouse-Thy-1.2, washed three times in medium, and then resuspended at $2 \times 10^6$ cells/ml in medium. The cells were then patch-clamped as described in the FIG. 1 legend. $CD_4^- CD_8^-$ Thy-1.2+ T cells were identified as green cells. Other T cells ($CD_4^+ CD_8^-$ Thy-1.2+, $CD_4^- CD_8$ +Thy-1.2+), were yellow, and B cells and monocytes ($CD_4^- CD_8^-$ Thy-1.2+) were unstained.

The mice used were: C57BL: 6 and 19 months; BALB/c: 1 and 7 months; BXSB-males: 2 mice aged 4 months; NZB x NZW: 2 mice aged 6 months, one aged 9 months; NZB x SWR: 3 mice aged 7-8 months; old MRL-+/+: 2 mice older than 20 months; NOD mice: 6 and 9 months; young MRL-+/+: 6, 10, and 12 months.

A. Assay for screening drugs

1) Studies on mouse lymphocytes a) Sacrifice of mice: Mice with autoimmune diseases (for example, systemic lupus erythematosus or type-1 diabetes mellitus) are sacrificed humanely by cervical dislocation after light anesthesia with metofane.

b) Isolating T cells from spleen, thymus or lymph nodes: The spleen, thymus, and lymph nodes are removed from the animal and single cell suspensions prepared by crushing the organ with the barrel of a syringe through a wire mesh. The cells are then washed three times with a cell sustaining medium, for example RPMI-1640 medium supplemented with heat inactivated fetal calf serum (10%), l-glutamine (1 mM), and appropriate antibiotics (for example penicillin/ streptomycin). The cells are then counted and resuspended at a concentration of $10 \times 10^6$ cells/ml. $50 \times 10^6$ cells are then placed on a nylon wool column to separate T cells from other blood cells as described previously in Grissmer, et al. *J. Immunol.* 41, 1137 (1988).

c) Staining: The T cells are incubated with anti-CD4 and anti-CD8 antibodies in the cold for an appropriate period (for example, 20-30 minutes), washed in the RPMI-1640 medium described supra, incubated in the cold with an appropriate dye-conjugated second antibody (for example, phycoerythrin-conjugated goat-anti-rat IgG antibody), washed in the medium described supra, and incubated in the cold with an appropriate dye-conjugated T cell specific antibody (for example fluorescein-conjugated anti-Thy-1.2, or anti-CD3, or anti-T cell receptor), washed with medium described supra, and then resuspended at $1$–$5 \times 10^6$ cells/ml in medium, and used for the experiments described below. The $CD_4^- CD_8^-$ T cells are then identified under the fluorescence microscope as cells expressing T cell-specific molecules like Thy-1.2, CD3 or T cell receptors, and not expressing the CD4 or CD8 molecules.

2) Studies on other animal systems

Similar approaches are used to isolate, identify and evaluate for exploitation according to this invention $CD_4^- CD_8^-$ T cells in other animal models, including humans, that express the CD4 and CD8 molecules in the immune system.

3) Studies on human cells a) Separation of cells from blood: Blood from patients with autoimmune diseases, for example, systemic lupus erythematosus are collected. Mononuclear cells are separated from the blood on a density gradient, for example, Ficoll-Hypaque. The mononuclear cells are washed with the medium described supra, and T cells isolated either by the nylon wool column method described supra, or by rosetting with sheep red blood cells as described in Chandy, et al., *J. Exp. Med.* 160, 369 (1984) or by any other standard method available. T cells are similarly isolated from available lymphoid tissues.

b) Staining: The cells are stained as described supra, first with anti-CD4 and anti-CD8, followed by an appropriate dye-conjugated second antibody, for example, phycoerythrin-conjugated goat-anti-mouse IgG antibody, followed by an appropriate dye-conjugated T-cell-specific antibody, for example, fluorescein-conjugated anti-CD3, or anti-CD2, or anti-T cell receptor, or anti-Leu-2. The $CD_4^- CD_8^-$ T cells are then identified under the fluorescence microscope as cells expressing T-cell-specific molecules like CD3 or CD2 or Leu-1 or T cell receptors, and not expressing the CD4 or CD8 molecules.

4) Electrophysiological recordings:

The cells are placed into a recording chamber and $CD_4^- CD_8^-$ T cells identified appropriately with an inverted microscope under fluorescent light, as described supra.. In cases where the predominant population of T cells is $CD_4^- CD_8^-$, for example, in lpr and gld mice or $CD_4^- CD_8^-$ cell lines, staining may not be required to identify the cells. These cells are studied electrophysiologically using the patch-clamp technique (Hamill, et al., *Pflugers Arch.* 391, 85 (1981).

a) Solutions: The cells under investigation are bathed in normal mammalian Ringer solution (160 mM NaCl, 4.5 mM KCl, 2.0 mM $CaCl_2$, 1.0 mM $MgCl_2$, 5 mM HEPES, adjusted to pH 7.4 with NaOH; 290 to 320 mosm). Other cell-sustaining solutions can also be used. The patch pipette contains an appropriate solution, for example: 134 mM KF, 11mM EGTA, 1 mM $CaCl_2$, 2 mM $MgCl_2$, 5 mM HEPES, adjusted to pH 7.2 with KOH; 285 to 310 mosm.

b) Identification of type 1 $K^+$ channels: By varying the voltage across the membrane, voltage-gated ion channels are opened and ion movement through these channels is measured as ionic current. Several distinct channel types have been characterized using a variety of electrophysiological techniques (Hille B: *Ionic channels of excitable membranes*, Sinauer Associates, Sunderland, Mass. (1984)). These channels are distinguished on the basis of electrophysiological and pharmacological criteria. Type 1 $K^+$ channels are identified in the patch-clamped cells on the basis of their inactivation properties, channel-closing kinetics, sensitivity to block by $TEA^+$, single channel amplitude, and voltage dependence of activation as described in detail by DeCoursey, et al., *J. Gen. Physiol* 89, 379 (1987).

c) Drug testing: After having identified the 1 type $K^+$ channels, the bathing solution is changed and replaced by a solution containing the drug of interest. The effect of the drug on the type 1 $K^+$ channels is monitored electrophysiologically, for example, changes of inactivation properties, or channel closing kinetics, or block , or shift in voltage dependence or activation, or alteration of single channel amplitude, etc. The same procedures are used to screen a battery of test materials on the same cell or on other cells containing type 1 $K^+$ channels. The selectivity of this drug to type 1 $K^+$ channels is determined by testing the effect of these test materials on other ion channel types, for example, type n $K^+$ channels in T cells. Drugs that modulate type l $K^+$ channels selectively and with great potency are identified. If the drug blocks the 1 channel the membrane depolarizes (becomes more positive because potassium channels control membrane voltage) and fluorescence of bisoxonal shifts measured by a spectrofluorometer. Bisoxonal, as an example of a membrane voltage-sensitive dye, is added to the cells expressing many type 1 channels prior to adding the drug candidate.

The patch clamping technique works similarly. Cells expressing many type 1 channels are patch-clamped. Drug candidate is added to the chamber containing cells to determine whether the channel is blocked. Replacement with a new candidate, repeating the process, allows screening of a number of candidates.

d) Preparation of antibodies against type 1 $K^+$ channels: The genes encoding type 1 $K^+$ channels are isolated by standard recombinant DNA techniques such as described in Weir, et al., Handbook of Experimental Immunology, Vol. 3 (1986) and other available documents. These genes are used as templates to prepare type l $K^+$ channel proteins or peptides, which are used as antigens to prepare antibodies against type 1 $K^+$ channels. A second method for preparing antibodies against type l $K^+$ channel is used with cells expressing large numbers of type l $K^+$ channels, isolating the cell surface proteins of these cells and using these proteins as antigens for the preparation of antibodies. The antibodies are screened for their ability to (a) effect type l $K^+$ channels electrophysiologically, as described supra, or (b) for their ability to destroy cells expressing type 1 $K^+$ channels, when the antibodies are conjugated to a cell toxin, or when the antibodies bind to the cell in the presence of complement, or (c) for the ability of radioisotope-, or dye-, or enzyme-linked antibodies to attach to the cells, attachment being monitored by fluorescence microscopy, by fluorescence cell sorting, by radioactive counting, or by enzyme-linked immunosorbent assays, or other appropriate techniques.

e) Drug and/or antibody testing in autoimmune disease: Drugs or antibodies identified by the assays described supra as being selective for type 1 $K^+$ channels are testing in vivo for efficacy in appropriate animal models, for example, for their ability to retard the onset and development of autoimmune diseases, or reverse autoimmune diseases. The route of administration of the drugs/antibodies can be oral, parenteral, or via the rectum, and the drug could be administered alone as principles, or in combination with other drugs or antibodies, and at regular intervals or as a single bolus, or as a continuous infusion in standard formations. Drugs or antibodies described supra are also tested in in vitro assays, for example, for their ability to stimulate B cells from autoimmune patients or animal models to secrete autoantibodies.

f) A treatment protocol: Drugs or antibodies identified by the assays described above are tested for safety in humans as per Federal regulations. Ordinary Phase 1 and 2 studies conducted pursuant to these regulations shall determine the safety and efficacious dose regimens appropriate in the circumstance for the treatment of the particular disease state of concern. These clinical studies are in the area of routine experimentation generally within the ken of the art-skilled. These drugs or antibodies described supra are administered via standard formulations to patients with autoimmune diseases, again either orally, parenterally, rectally, alone or in combination, at regular intervals or as a single bolus, or as a continuous infusion, for modulating type 1 K+ channels in the $CD_4^-CD_8^-$ T cells thereby abrogating their abnormal accessory helper function and impacting on the course of the autoimmune disease.

B. Other Murine Autoimmune Disorders:

Mice

DBA-J/Lac-J male mice were purchased from the Jackson Laboratory (Bar Harbor, ME). They were injected intradermally near the base of their tails with 100 ug of highly purified chick type II collagen emulsified in complete Freunds Adjuvant (CFA) that contained additional *Mycobactrium butyricum* (Difco). The collagen/CFA emulsion was prepared by adding 1 volume of modified CFA (30 ug of *M. butyricum* per 50 ul of 0.01N acetic acid). Animals were immunized with 100 ul of this mixture using a 26 gauge needle. One group of control animals was not injected and another group was injected with modified CFA without collagen. Five mice developed clinically evident arthritis with enlarged, inflamed paws. These mice had arthritic involvement of one paw, and two had arthritis of two paws. Paw thickness was measured with a Schnelltaster constant-tension caliper. The type II collagen was prepared from chick sternal cartilage by established methods. Miller, *Biochemistry* 10, 1652 (1971). Two mice injected with type II collagen and CFA did not develop obvious signs of arthritis; mice injected with collagen were killed 10 to 12 weeks after immunization for patch-clamp studies.

*E. coli* (ATCC 8739, wild type) was homogenized in a Manton-Gaulin homogenizer at 6000 psi for 5 min, and heat-inactivated for 30 min at 60° C. The bacteria were then adjusted to a concentration of 0.5 mg/ml stock in phosphate buffered saline (PBS). BALB/c mice were then immunized intraperitoneally with 1 ml of solution containing 0.5 ml antigen (15 ug. *E. coli*) in PBS and 0.5 ml CFA. Mice received booster injections of antigen (15 ug *E. coli*) and incomplete Freund's adjuvant 4 weeks and 6 weeks later. Mice were sacrificed 1 week after the second booster immunization.

(2) Antibodies: PE-conjugated-anti-CD4 (L3T4), FITC-conjugated-anti-CD8, FITC-conjugated-anti-Thy-1,2, anti-CD4 and anti-CD8 were purchased from Becton Dickinson (Mountain View, Calif.). PE-conjugated-goat-anti-rat IgG (affinity purified and absorbed against mouse IgG) were purchased from Caltag (Rupp and Bowman, Tustin, Calif.).

(3) Separation of T Cells: Mice were killed, and single-cell suspensions were prepared from the spleen. T cells were enriched by passage through a nylon wool column. Cells were then suspended in RPMI-1640 medium supplemented with 10% heat-inactivated FCS (Hyclone, Logan, Utah) and 2 mM 1-glutamine (medium).

(4) Staining: Cells ($2 \times 10^6$) were incubated with an appropriate dilution of anti-CD4-PE and anti-CD8-FITC for 30 min on ice, washed three times with medium, and resuspended in 1 ml of medium. The stained cells were plated into glass chambers, and the $CD_4^-CD_8^-$ appear orange) and $CD_4^-CD_8^+$ (green) were identified by epifluorescence microscopy. To identify $CD_4^-CD_8^-$ T cells, cells were incubated with anti-CD4 and anti-CD8 for 30 min on ice, washed three times with medium, incubated with PE-labeled-goat-anti-rat IgG for 30 min on ice, washed five times with medium incubated with FITC-labeled-anti-Thy-1.2 for 30 min on ice, washed three times with medium, and then resuspended in 1 ml of medium. The cells were visualized under the microscope and three populations were evident: $CD_4^-CD_8^-$ Thy-1.2$^+$ cells appeared green, $CD_4^+CD_8^-$ Thy-1.2$^+$ and $CD_4^-CD_8^+$ Thy-1.2$^+$ cells appeared yellow, and B cells and macrophages were unstained. These staining protocols do not affect channel expression (Chandy, et al., *Eur. J. Immunol.* (in press); Lewis and Cahalan, *Science* 239, 771 (1988); Grissmer, et al., *J. Immunol.* 141, 1137 (1988)). In most experiments, chambers were coated with polylysine (0.25 mg/ml) to improve cell adherence to the dish. This procedure did not alter channel expression when compared with cells plated into uncoated chambers.

(5) Electrophysiology: After phenotypic identification by epifluorescence microscopy, single T cells were patch-clamped at room temperature (22° to 26° C). Details of the giga-ohm voltage-clamp technique used here are described elsewhere (Chandy, et al., *Eur. J. Immunol.* (in press); Lewis and Cahalan, *Science* 239,771 (1988); Grissmer, et al., *J. Immunol.* 141, 1137 (1988); Chandy, et al., *Science* 233, 1197 (1986); Cahalan, et al., *J. Physiol.* 358, 197 (1985)).

Solutions: The cells under investigation were bathed in normal mammalian Ringer solution containing (in mM): 160 NaCl, 4.5 KCl, 2 MgCl$_2$, 1CaCl$_2$, and 5 Na-HEPES (pH 7.4). The patch pipette contained 134 KF, 11 K$_2$-EGTA, 1.1 CaCl$_2$, 2 MgCl$_2$ and 10 K-HEPES (pH 7.2). In Ringer solutions containing tetraethylammonium chloride (TEA$^+$), NaCl was replaced by the appropriate TEA$^+$ concentrations keeping the osmolarity constant. The bath solution could be changed during recordings by bath perfusion.

Identification of K$^+$ channel type: K$^+$ channels were identified on the basis of their inactivation properties, channel closing kinetics, and sensitivity to block by TEA$^+$ (Lewis and Cahalan (1988), *Science* 239, 771; Grissmer, et al. (1988), *J. Immunol.* 141, 1137; Chandy, et al. (1986), *Science* 233, 1197; DeCoursey, et al. (1987), *J. Gen. Physiol.* 89, 379; DeCoursey, et al. (1987), *J. Gen. Physiol.* 89, 405). Type n K$^+$ channels are use-dependent, close slowly upon repolarization with a time constant of about 30 ms at $-60$ mV and are blocked by TEA$^+$ ($K_D$=8mM). Type l K$^+$ channels are not use-dependent, close more rapidly on repolarization with a time constant of 2 ms at $-60$mV, and are much more sensitive to block by TEA+ ($K_D$=0.1 mM). Type n' K+ channels are not use-dependent, close slowly as do type n K+ channels upon repolarization, but are less sensitive to block by TEA+ ($K_D$—100 mM).

Determination of maximal K+ conductance ($g_k$) and number of K+ channels per cell. $g_k$ was calculated from the largest K+ current recorded in each cell. A reversal potential of −80 mV was used to calculate $g_k$ (Cahalan, et al., *J. Physiol.* 358, 197 (1985). The number of K+ channels per cell was calculated by dividing $g_k$ by the single-channel conductances of the appropriate channel type; the single-channel conductances are 18, 27, and 17 pS for n, l and n', respectively (Chandy, et al. *Eur. J. Immunol.* 20, 747 (1990); Lewis and Cahalan *Science* 239, 771 (1988); Grissmer, et al. *J. Immunol.* 141, 1137 (1988); and Grissmer, et al., *J. Immunol.* 145, 2105 (1990)).

Murine SLE is associated with altered K+ channel in $CD_4^-CD_8^-$ Thy-1.2+ T cells, irrespective of the genetic background of the mouse.

K+ channel expression was investigated in mAb-defined T cell subsets from genetically distinct murine models for SLE with varied clinical features and immunological abnormalities. FIG. 1a shows K+ outward currents in splenic and $CD_4^-CD_8^-$ cells from normal mice and from mice with SLE. In these experiments, the membrane potential of the cells was held at −80 mV, and then depolarizing pulses were applied to +40 mV. This protocol opens all the voltage-gated K+ channels in the cell. The normal mouse (BALB/c) $CD_4^-CD_8^-$ cell shows small voltage-gated K+ currents which are half-blocked by 10 mM tetraethylammonium (TEA+), indicating that it expresses low numbers of type n K+ channels. The $CD_4^-CD_8^-$ cell from the mouse with SLE (N2B x NZW) $F_1$ displays large K+ currents which are half-blocked by 0.1 mM TEA+ indicating that this cell possesses many type l K+ channels.

FIG. 1b demonstrates the maximum K+ conductance, $g_k$, of splenic DN cells from normal mice and mice with SLE, $CD_4^-CD_8^-$ cells of three normal strains of mice (C3H, C57BL, BALB/c) express small numbers (10-20 K+ channels/cell) of types n, l, or n' K+ channels. In marked contrast, 68 of 76 phenotypically similar cells from 7 murine models for SLE [(NZB X NZW)$F_1$ (NZB x SWR)$F_1$, BXSB-Yaa, MRL-+/+, MRL-lpr, C3H-lpr, C3H-gld] expressed exclusively type l K+ channels in lprlgld mice expressed the alpha/-beta (F23.1+) TcR α/β. Occasionally we observed cells with small numbers of type n K+ channels; these may be normal $CD_4^-CD_8^-$ cells. Helper ($CD_4^-CD_8^-$) and cytotoxic ($CD_4^-CD_8^-$) T cells from mice with SLE displayed a small number of K+ channels like helper and killer T cells from normal mice. Thus, SLE is associated with the augmented expression of type l K+ channels in $CD_4^-CD_8^-$ cells, regardless of the genetic background of the mouse or the clinical and immunological features that may be unique to a particular strain.

Altered K+ channel expression in $CD_4^-CD_8^-$ cells parallel the development of disease.

FIG. 2 demonstrates that $CD_4^-CD_8^-$ T cells from young MRL-+/+ mice, prior to the onset of autoimmunity, displayed about 10 K+ channels/cell which were types n, l, or n', a pattern similar to that of T cells from normal mice. Older MRL-+/+ mice with lupus nephritis expressed ~200 type l K+ channels/cell. Similar results were obtained in $CD_4^-CD_8^-$ T cells from young and old lpr mice (FIG. 2). These data suggest that elevation of type 1 K+ channel expression in $CD_4^-CD_8^-$ cells parallels the development of SLE. Interestingly, $CD_4^-CD_8^-$ cells from diseased SLE mice induce B cells to secrete cationic anti-DNA autoantibodies in vitro whereas phenotypically similar cells from lupus-prone mice, prior to the onset of disease, do not exhibit this property. The development of lupus nephritis appears to be dependent on the deposition of the cationic IgG anti-double-stranded autoantibodies on the negatively charged glomerular basement membrane.

$CD_4^-CD_8^-$ cells from diseased non-obese diabetic (NOD) mice with type-1 diabetes mellitus possess numerous type l K+ channels.

The only other known model for spontaneously developing autoimmune disease is the non-obese diabetic mouse that progressively becomes diabetic with age, apparently due to T-cell-mediated destruction of pancreatic islet cells. The clinical features of diabetes in these mice resemble human type-1 diabetes mellitus. To determine whether altered ion channel expression in $CD_4^-CD_8^-$ cells links SLE and other autoimmune diseases, we examined splenic $CD_4^-CD_8^-$ cells from NOD mice which had clinical evidence of diabetes. Interestingly, the majority of $CD_4^-CD_8^-$ cells from diabetic NOD mice exhibit large numbers of type l K+ channels, averaging 200 channel/cell (FIG. 3). A few cells (4/21) displayed small numbers of K+ channels and may represent normal cells. Hence, elevated numbers of type / K+ channels in $CD_4^-CD_8^-$ cells are a characteristic of both type-1 diabetes mellitus and SLE.

Chronic EAE (a model for multiple sclerosis) is associated with abundant type l K+ expression in $CD_4^-CD_8^-$ T cells.

Observations were extended to genetically determined models for autoimmune disease to an acquired autoimmune disorder. Inoculation of SJL/P1J mice with myelin basic protein induces an immune response, leading to demyelination and acute EAE. Some mice progress into a chronic relapsing form of encephalomyelitis (chronic EAE) which resembles multiple sclerosis in humans. $CD_4^-CD_8^-$ cells from mice with acute EAE had normal K+ channel expression. In contrast, 10 of the 21 splenic cells examined from mice with chronic EAE had an average of ~200 type l K+ channels/cell, similar to $CD_4^-CD_8^-$ cells from mice with SLE and type-1 diabetes mellitus (FIG. 3). The remaining cells had few K+ channels and may represent normal cells.

Isolation of mouse and human gene sequences which encode the type l K+ channel.

K+ Channel Nomenclature

Several vertebrate voltage-gated K+ channel genes have been isolated and have frequently been given inconsistent names. Recently, a simplified nomenclature has been proposed for this family of genes based on sequence relatedness to the Shaker, Shab, Shaw and Shal genes in Drosophi/a (Chandy et al. (1991) *Nature* 352, 26. The mKv3.1b cDNA described herein is the mouse homologue of the rat Kv3.1 b (rKv3.1 b) transcript previously described by Luneau et al. (1991) *Proc. Natl. Acad. Sci. USA* 8,3932.

Isolation of the mKv3.1b cDNA: Approximately 7×10$^5$ plaques of a mouse brain cDNA library (cDNA partially digested with EcoRI and cloned into lambda gt10, a gift of Dr. Daniel Littman, UCSF, San Francisco, Calif.) were screened with a mixture of Kv3.3

5′(1.0 kb Bam/Sac), Kv3.3 3′(2.2 kb Pst), and Kv3.4 3′(1.1 kb HindIII/BglII) probes labeled with 32 P to a specific activity of $1.2 \times 10^9$ cpm/μg with the random primer method (Feinberg and Vogelstein (1983) *Anal. Biochem.* 132, 6. Hybridization was performed at 55° C. in hybridization buffer for 16–18 hours. Hybridization buffer contains 5×SSC (1×SSC is 0.15M NaCl, 0.15M sodium citrate), 10×Denhardt's (0.2% bovine serum albumin, 0.2% Ficoll, 0.2% polyvinyl pyrrolidone), and 0.1% sodium dodecyl sulphate (SDS). The blots were washed at a final stringency of 0.5×SSC and 0.1% SDS for 60 min at 53° C. DNA was isolated from the hybridizing lambda phage clone, 382, digested to completion with EcoRI, and electrophoresed in a 1% agarose gel. The resulting EcoRI cDNA fragments (1.9 kb and 0.87 kb) were subcloned into M13mp19 and pBluescript II KS+ vectors (Stratagene, La Jolla, Calif.) and sequenced by the dideoxy chain termination method (Sanger et al. (1977), *Proc. Natl. Acad. Sci. USA* 74, 5463) using a Sequenase kit (U.S. Biochemical, Cleveland, Ohio).

Construction and Expression of mKv3.1b cRNA in Xenopus Oocytes: The mKv3.1b coding region was inserted into the pBluescript II KS+ cloning vector using a three-way ligation as follows: The upstream 0.87 kb EcoRI fragment of the cDNA was digested with NarI (7 bp upstream of the ATG initiation codon) and EcoRI (814 bp into the coding region) to generate an 820 bp fragment. The downstream 1.9 kb EcoRI fragment was digested with EcoRI (814 bp into the coding region) and PstI (57 bp beyond the stop codon) to generate a 995 bp fragment. The two mKv3.1 b fragments were then inserted into the ClaI (compatible restriction overhang with NarI) and PstI sites of a pBluescript II KS+ vector which had a 200 bp poly(A)+ stretch inserted between NotI and SacII in the polylinker. The resulting 1,815 bp NarI/PstI insert was verified by restriction mapping and the integrity of the splice sites were confirmed by double-stranded DNA sequencing. For transcription, the plasmid was linearized by digestion with SacI in the polylinker. RNA was transcribed using the T3 promoter in pBluescript II KS+ and injected into oocytes as described previously (Grissmer et al. (1990), Proc. Natl. Acad. Sci. USA 85, 7652).

Electrophysiology.

Experiments were carried out on Xenopus oocytes with two-electrode voltage-clamp and patchclamp techniques (Hamill et al. (1981), Pflugers Archiv. 391, 85). All experiments were done at room temperature (22°–26°C.).

For the two-electrode voltage-clamp experiments, cells were bathed in oocyte Ringer solution containing 96mM NaCl, 2 mM KCl, 1.8 mM $CaCl_2$, 1 mM $MgCl_2$, 5 mM N-2-hydroxyethylpiperazine-N′-2-ethanesulfonic acid (HEPES), and adjusted to pH 7.5 with NaOH. The pipette solution was 3 M KCl. Patch-clamp experiments were carried out under identical conditions in oocytes and in T cells, using a mammalian Ringer solution containing 160 mM NaCl, 4.5 mM KCl, 2 mM $CaCl_2$, 1 mM $MgCl_2$, 5 mM HEPES, and adjusted to pH 7.4 with NaOH and a total osmolarity of 290–320 mosm/kg. Internal (pipette) solutions contained: 140 mM KF, 2 mM $MgCl_2$, 1 mM $CaCl_2$, 5mM HEPES, 11 mM $K_2$-ethylene glycol-bis(β-aminoethylether)N,N,N′,N′-tetraacetic acid (EGTA). CTX was purchased from Latoxan (IBF-Biotechnics, Inc., Columbia, Md.).

The patch-clamp amplifier (List L/M-EPC 7, Adams and List Associates, Ltd., Great Neck, N.Y.) was used in the voltage-clamp mode without series resistance compensation. Patchclamp electrodes were pulled from Accu-fill 90 Micropets (Becton, Dickinson & Co., Parsippany, N.J.) in three stages, coated with Sylgard (Dow Corning Corp., Midland, Mich.) and fire-polished to resistances, measured in the bath, of 2–7 MΩ. In all patch-clamp experiments, the command input of the patch-clamp amplifier was controlled by a PDP 11/73 computer via a digital-analog converter, and membrane currents were recorded at a bandwidth of 2 kHz. The holding potential was adjusted in all experiments to $E = -80$ mV. Correction for capacitative currents was achieved by analog subtraction.

Oligonucleotide Primers: Synthetic oligonucleotide primers were prepared (ChemGenes Corp., Needham, Mass.) from the coding regions of mKv3.1a. The upstream and two downstream primers were 1) 5′-GAAATCGAGAAGCTTCGAAACGG-3′(SEQ ID NO: 1), which lies between the S1–S2 loop, 2) 5′-CAG-GAAGATGATCAGCTGCAGG-3′(SEQ ID NO: 2), lying in the S5 transmembrane region, and 3.) 5′-GTGTGGAGAGTTAACGACAG-3′(SEQ ID NO: 3), prepared from a region 112 bp downstream of S6.

PCR Amplification of mKv3.1 from RNA from MRL-lpr T cells and human Louckes lymphoma cells: Total RNA isolated from the lymph nodes of diseased MRL-lpr mice and from human Louckes cells was used to generate a random-primed cDNA product as previously described (Grissmer et al. (1990), Proc. Natl. Acad. Sci. USA 87,9411). The 20 μl reaction mixture contained 48 units AMV reverse transcriptase (U.S. Biochemicals, Cleveland, Ohio), 20 units RNASin (Boehringer Mannheim Biochemicals, Indianapolis, Ind.), 100 pM random 14-mer nucleotide mixture (Boehringer Mannheim), 1 μg total RNA (5 μl), and 1 mM each of dNTP's (GeneAmp Kit, Perkin-Elmer-Cetus, Norwalk, Conn.). cDNA synthesis was then initiated by the random-primer method (Krug and Berger (1987), *Methods in Enzymology* 152, 316). The cDNA product was amplified by PCR for 33 cycles (annealing temperature 55° C.) with Taq polymerase (GeneAmp Kit) using the upstream (primer 1) and downstream (primer 3) primers. The reaction mixture contained 1 mM of each dNTP, 100 pM of each of the primers and 5 μl of the cDNA template. As a control for contaminating genomic DNA, 5 μl of RNA (lpr and Louckes) without cDNA synthesis was run in parallel PCR reactions. The amplified product (65 μl) was then run on a 1.5% agarose gel in TAE buffer. Based on the mKv3.1a sequence (Yokoyama et al. (1989), FEBS Lett. 259, 37) the amplified product would have a predicted size of 774 bp. The resulting 774 bp PCR product was next primed with the 5′ oligo in the S1–S2 loop (primer 1) (SEQ ID NO: 1) and the internal oligonucleotide in the S5 segment (primer 2) (SEQ ID NO: 2) to amplify a second PCR product with a predicted size of 390 bp. The 774 bp PCR fragment from Louckes cells was cloned into pBluescript and single-stranded phage was generated and sequenced by the dideoxy chain termination method. Single-stranded DNA prepared from the 774 bp fragment amplified from MRL-lpr T cells using the asymmetric PCR method (Gyllensten and Erlich (1988), *Proc. Natl. Acad. Sci. USA* 87, 9411) was similarly sequenced. In addition to the oligonucleotide primers described above, we used one other primer (5′-AAAGTGCGTGTGCTCACTGG-3′) (SEQ ID NO: 4) from the middle of the 774 bp fragment for the asymmetric PCR experiments and for sequencing.

Chromosomal Localization: A mKv3.1b coding region probe (1.7 kb EcoRI fragment) was labeled to a specific activity of 1 cpm/μg by the random primer method and then used for the chromosomal studies. Chromosomal assignments for Kv3.1 were determined by Southern-blot analysis (genomic DNA digested with EcoRI) of a panel of 59 human-chinese hamster cell hybrids (Ghanshani et al. (1992), *Genomics* 12, 190). We also examined HindIII-digested genomic DNA from these cell lines to resolve any ambiguities. In all experiments, the probes were also hybridized separately to either hamster or human genomic DNA digested with EcoRI or HindIII. The Kv3.1-hybridizing hamster and human bands were readily distinguished on the basis of size. The hybrids were isolated using a variety of selectable markers (Cirullo eta. (1983) *Somatic Cell Genet.* 9, 215; Overhauser et al. (1987), *Nucleic Acids Res.* 15, 4617). All hybrids were characterized cytogenetically by trypsin-Giemsa banding and G-11 staining to determine which human chromosomes were retained. The analyses were repeated at the time the cells were harvested for the preparation of DNA. In all cases, twenty metaphase chromosome spreads were examined. Hybridization was performed at a final stringency of 65° C. and 0.1×SSC for 30 min to avoid cross-hybridization with related genes.

A human genomic clone (#361) encoding Kv1.1 was isolated, and a 4 kb HindIII fragment from this clone was used to probe the DNA panel at high stringency (65° C., 0.1×SSC). A 1.5 kb EcoRI fragment from the coding region of mouse Kv3.2 (clone # MShaw 12; gift from Michael Pak and Lawrence Salkoff, Washington University, St. Louis, Mo.) was similarly used for chromosomal mapping. A 420 bp EcoRI-HindIII fragment from the coding region of the rat IsK (MinK) gene (gift from Richard Swanson, Merck Sharpe and Dohme, West Point, Pa.) was also used for chromosomal localization studies.

RESULTS

CD4−CD8− T cells from mice with type II collagen arthritis disease (a model for rheumatoid arthritis) possess abnormally large numbers of type l K+ channels.

FIG. 4a shows the maximum K+ conductance or $g_{Kmax}$ of splenic CD4−CD8− cells from normal and diseased mice, and FIG. 4b represents the fraction of cells with large numbers of type l K+ channels. The upper limit for the $g_k$ of CD4−CD8− cells from normal DBA/l-LacJ mice, is 1000 picosiemen (pS), with an average of 299±78 pS. The $g_k$ of CD4−CD8− cells from three other normal strains of mice (C3H-HeJ, BALB/c and C57BL) are shown for comparison ($g_k$=405±53 pS; mean±53 pS; mean±SEM; n=51). These data indicate that normal CD4−CD8− T cells express roughly 10–20 K+ channels/cell of types n, l or n'. In marked contrast, 14 out of 34 CD4−CD8− cells from diseased DBA/1-LacJ mice immunized with type II collagen, exhibited a $g_k$ greater than 1000 pS (FIG. 4a and 4b), and the channels in these cells were exclusively type l, averaging 180 channels/cell. Interestingly, CD4−CD8− cells exhibiting large numbers of type l K+ channels were substantially fewer (3/25) in DBA/1-LacJ mice immunized with type II collagen with no obvious clinical signs of arthritis (FIG. 4a and 4b) compared with mice with obvious disease. These data show that elevation of type l K+ channel expression in CD4−CD8− cells parallels the development of collagen arthritis.

Other T-cell subsets from diseased mice retain their normal pattern of expression. FIG. 5 shows the $g_k$ of helper (CD4+CD8−) and cytotoxic (CD4−CD8+) T cells from normal and diseased mice. CD4+CD8− T cells from both normal and diseased mice exhibited small number of K+ channels, (averaging 10–20 channels per cell), which were predominantly type n. CD4−CD8− T cells from mice with collagen arthritis displayed small numbers of types n' or l K+ channels like their phenotypic counterparts from normal mice. Thus, the augmentation of type l K+ channel numbers associated with arthritis, appears to be a feature confined to CD4−CD8− cells. Similar results were found in mice with lupus, diabetes and EAE.

Abundant type l K+ channel expression in CD4−CD8− T cells is not a feature of a generalized immune response in vivo. To discern whether the enhanced numbers of type l K+ channels in CD4−CD8− cells were unique to autoimmune disorders, or whether it reflected a generalized immune response in vivo, CD4−CD8− cells were examined from mice immunized with either heat-killed *E. coli* or complete Freund's adjuvant CFA (FIG. 6). Mice received either one CFA immunization (26 days before patch-clamp experiments) or booster doses of CFA either 62 or 26 days before or 26 and 2 days before patch-clamp experiments. CD4−CD8− T cells from these mice possessed small numbers of types n, l or n' channels, regardless of whether they received one immunization or booster doses. Since T cells activated by mitogens in vitro, enlarge (have an average membrane capacitance >2 pF corresponding to a cell diameter >8 um), we compared $g_k$ of large (>2 pF) and small (<2 pF) CD4−CD8− cells in CFA immunized mice. $g_k$ of large cells (580±170 pS; mean±SD; n=5) was not significantly different from that of small cells (500±275 pS; mean±SD; n=27). Similarly, CD4−CD8− cells from mice immunized with heat-killed *E. coli* also display small numbers of K+ channels of one of the three types. Taken together these data show that expression of a high number of type l K+ channels by CD4−CD8− T cells is associated with symptoms of autoimmune diseases.

FIG. 7 shows K+ outward currents in CD4−CD8− cells from normal DBA/1-LacJ mice and mice with collagen arthritis. In the experiments shown in the upper panel, the decline in the size of the K+ current elicited by a repetitive (1/s) depolarizing voltage-step from −80 mV to +40 mV for a duration of 200 ms was measured. This property of K+ channels which is termed use dependence is characteristic of type n K+ channels, but not of type l or n'. Another feature of type n K+ channels is their closing kinetics during membrane hyperpolarization, after an initial period of depolarization. This property is called deactivation or tail currents is shown in the bottom panel of FIG. 7. In these studies, the membrane potential was held at −80 mV, then stepped to +40 mV for a 15 ms duration to open all the channels, and then stepped back to either −30 or −60 mV. Type n and n' channels close slowly (time constants for closure are 75 ms and 40 ms at −30 mV and −60 mV, respectively), whereas the l K+ channels close rapidly (time constants for closure are 6 ms and 2 ms at −30 mV and −60 mV, respectively.

Normal CD4−CD8− cells (left panel of FIG. 7) have small K+ currents that are use-dependent (top), display slow deactivation kinetics (bottom), are half-blocked by 10 mM TEA+ (not shown), indicating that they express small numbers of type n K+ channels. CD4−CD8− T cells from diseased mice have large K+ currents (right panel of FIG. 7) that are not use dependent (top), exhibit rapid deactivation kinetics (bottom), are half-blocked by 0.1 mM TEA+ (not shown), indicating that these cells express an abundance of type 1 K+ channels.

Isolation and characterization of mouse and human clones encoding the type 1 K+ channel.

Mouse Kv3.1b Expression in Oocytes: Xenopus oocytes express a high density of voltage-activated K+ channels following injection of mKv3.1b mRNA. With two-electrode voltage clamping, currents in excess of 15 μA at test potentials of +40 mV, representing on the order of $10^7$ channels, were routinely observed following injection of 0.5 ng of mRNA (50 nl at 0.01 μg/μl, not shown). Single channel recordings were done on outside-out patches from these oocytes, whereas gating and inactivation kinetics and pharmacological sensitivities were determined using outside-out patches of oocyte membrane injected with a 10 times more concentrated mRNA solution (50 nl of 0.1 μg/μlmRNA).

Reflecting the large currents seen in microelectrode recordings from the whole oocyte, current magnitudes in excised patches were large, sometimes representing more than a thousand channels per patch.

Voltage-Dependence of the mKv3.1b Gene Product: Oocyte mKv3.1b patch currents were very similar to whole-cell K+ currents in normal mouse cytotoxic T lymphocytes (Lewis and Cahalan, (1988) Science 239, 771) in abnormal CD4−CD8− (double-negative, or DN) T cells from several mouse models of autoimmune disease (Chandy et al., (1986) Science 233,1197 and (1990) Eur. J. Immunol. 20, 747; DeCoursey et al., (1987) J. Gen. Physiol. 89, 379; Grissmer et al., (1988) J. Immunol. 141, 1137 and (1990) J. Immunol. 145, 2105) and in the human B-lymphoma line, Louckes (Shapiro and DeCoursey, (1988) Biophys. J. 53, 550a; see below). Table I compares several gating properties of the mKv3.1b gene product, expressed in oocytes, with properties of type 1 K+ channels in mouse T cells and in the human Louckes cells. Gating properties of the type n channels in human T cells, and those of the cloned mKv3.1a and rKv3.1b gene products expressed in oocytes, are included in Table I for comparison. For these determinations, identical solutions at mammalian ionic strength (290–320 mosm/kg) were employed. FIG. 8 illustrates records and analysis of K+ currents from oocytes expressing the mKv3.1b gene product. The outward currents appear to represent a single population of K+ channels which become activated at depolarizing potentials positive of about −20 Vm. Upon depolarization, the channels open with a sigmoid time course, reach a peak within about 10 ms, and inactivate slightly. From the conductance-voltage relation shown in FIG. 8B, the midpoint of channel activation is ~0 mV. This value is characteristic of type 1 K+ currents recorded in the whole-cell configuration from normal mouse cytotoxic T cells (Lewis and Cahalan, (1988) Cell Regulation 1, 99) from abnormal CD4−CD8− T cells taken from ten mouse models of autoimmunity (Chandy et al., (1986) Science 233, 1197 and (1990) Eur. J. Immunol. 20, 747; DeCoursey et al., (1987) J. Gen. Physiol. 89, 379; Grissmer et al., (1988) J. Immunol. 141, 1137 and (1990) J. Immunol. 145, 2105), and from human Louckes lymphoma cells (Table I). Thus, the voltage dependence for K+ channel activation of mKv3.1b currents matches that of type 1 K+ currents in both human and mouse lymphocytes.

TABLE I

Gating parameters of Kv3.1 K+ currents expressed in oocytes.
Type 1 and type n K+ current properties in lymphocytes are included for comparison.

| Channel | $V_n$ (mV) | Gating $k_n$ (mV) | $\tau_h$ at 40 mV (ms) | $\tau_{tail}$ at −60 mV (ms) | Single-channel conductance γ (pS) |
|---|---|---|---|---|---|
| Cloned 1 channels | | | | | |
| [1]mKv3.1b cDNA | −1 | −11 | 630 | 2.5 | 27 |
| [2]mKv3.1a cDNA (NGK2) | 16 | −9 | n.d. | n.d. | 26 |
| [3]rKv3.1b cDNA (Kv4) | 15 | −10 | n.d. | n.d. | n.d. |
| Native channels | | | | | |
| [1]type 1 (human) | −4 | −12 | 565 | 1.4 | 26 |
| [4]type 1 (mouse) | −9 | −9 | 340 | 2.6 | [6]21, [6]27 |
| [5]type n (human) | −36 | −4.3 | 178 | 44 | [7]9, [7]16 |
| [4]type n (mouse) | −36 | −7.3 | 107 | 49 | [6]12, [6]18 | n.d. not determined
[1]data from this paper, numbers represent the mean of 3-5 determinations.
[2]data from Yokoyama, et al., 1989
[3]data from Luneau, et al., 1991
[4]data from DeCoursey, et al., 1987
[5]data from Cahalan, et al., 1985
[6]Mouse type n and type 1 channels each exhibit only one single channel conductance state which has been variously reported to be 12 and 18 pS for type n, and 21 and 27 pS for type 1 (DeCoursey, et al., 1987; Lewis and Cahalan, 1988).
[7]In human T cells two distinct single—channel events have been described with conductances of 9 and 16 pS; these may represent two types of channels, or one channel with two conductance states (Cahalan, et al., 1985).

Activation and Inactivation Kinetics.

Kinetic properties of activation and inactivation are also similar between mKv3.1b channels and 1 type currents from mouse and human lymphocytes (Table I). The time course of K+ currents in five oocyte patches was analyzed using a modified Hodgkin-Huxley kinetic model with activation (n4) and inactivation (h); no particular microscopic mechanism for gating is implied by this quantitative description. The rates for channel activation and inactivation are similar to those reported previously for type 1 channels (FIG. 9, Table I). Channel inactivation, in particular, provides a convenient property to distinguish between diverse types of K+ channels. In contrast to "use-dependent" inactivation characteristic of type 1 K+ channels, inactivation of type 1 K+ channels does not accumulate during repetitive depolarizing pulses delivered at 1 Hz. The time course of inactivation and lack of use-dependence exhibited by mKv3.1b K+ currents expressed in oocytes are similar to those for type 1 channels in mouse T cells and in human Louckes cells (FIG. 10, Table I).

Closing Kinetics.

The kinetics of K+ channel closing can be determined by first opening the channels with a 15 ms conditioning pulse to +40 mV, and then forcing the channels to close by repolarizing to different potentials (FIG. 11). The time constants, τt, of the resultant "tail currents" are plotted against the repolarized membrane potential. The closing rate for K+ channels increases at more negative potentials. Typically, at −60 mV the tail current time constant is between 1-3 ms. Similar tail current time constants have been described for type 1 K+ channels in lymphocytes (Table I; DeCoursey et al. (1987) ibid.; Lewis and Cahalan, (1988) ibid; Grissmer et al., (1988) ibid and (1990) *J. Immunol.* 145, 2105; Chandy et al., (1990) *Eur. J. Immunol.* 20, 747). This provides support for the proposition that the mKv3.1b gene product expressed in oocytes encodes the type 1 K+ channel found in T lymphocytes. In contrast, type 15 channels close about 20-fold more slowly (Table I).

Pharmacology.

Pharmacological blocking agents provide a further test for classification of K+ channels. Type 1 channels from normal mouse cytotoxic T cells (Lewis and Cahalan, (1988) ibid.), from abnormal MRL-lpr mouse CD4−CD8− T cells (Chandy et al. (1986) *Science* 233,1197; DeCoursey et al. (1987) ibid.; Grissmer et al. (1988) ibid. and (1990) *J. Immunol.* 145, 2105; Chandy et al. (1990) *Eur. J. Immunol.* 20, 747) and from human Louckes lymphoma cells (Table II), are highly sensitive to block by TEA, with a half-blocking dose of 0.1 mM. The mKv3.1b mRNA currents exhibit the same high level of TEA sensitivity (FIG. 12, Table II), as do the expression system (Table II). 4-aminopyridine (4-AP) blocked mKv3.1b K+ currents with a half-blocking dose of 180 μM. Quinine, and verapamil increased the apparent rate of mKv3.1b K+ current inactivation, and produced "use-dependent" block. These results closely resemble the pharmacological profiles of type 1 K+ channels from mouse lymphocytes (DeCoursey et al. (1987) ibid.) and human Louckes lymphoma cells, although these agents have similar effects on type n channels (DeCoursey et al. (1985) and (1987) ibid.).

Block by polyvalent cations and scorpion toxins can further distinguish specific K+ channel types. $La^{3+}$ and $Co^{2+}$ strongly shift the voltage dependence of activation to more depolarized potentials, with minimal blocking, of type 1 K+ channels from MRL-lpr mice (DeCoursey et al (1987) ibid.). Both cations had similar effects on mKv3.1b currents expressed in oocytes (Table II). In contrast, type n channels are strongly blocked by these polyvalent cations. CTX has been shown to block types n and n' K+ channels with nanomolar affinity, while having no effect on type 1 channels from mouse lymphocytes and human Louckes lymphoma cells (Lewis and Cahalan (1988) ibid.; Sands et al. (1989) *J. Gen. Physiol.* 93, 1061; Grissmer et al. (1992) *J. Gen. Physiol.* 99, 1, Table II). The mKv3.1b K+ currents were resistant to high doses of CTX. The pharmacological properties of mKv3.1b and type 1 K+ channels in mouse T cells and human Louckes cells are therefore notably similar.

TABLE II

Pharmacological properties of Kv3.1 K+ currents expressed in oocytes. Type 1 and type n K+ current properties in lymphocytes are included for comparison.

| | Blockers | | | | | [2]Effect of 20 mM $Co^{2+}$ (*10 mM) | |
| --- | --- | --- | --- | --- | --- | --- | --- |
| | | | | | | shift | |
| Channel | TEA (mM) | 4-AP (mM) | quinine (μM) | verapamil (μM) | CTX (nM) | $\Delta E_n$ (mV) | block gK(Co)/gK |
| Cloned 1 channels | | | | | | | |
| [1]mKv3.1b CDNA | 0.15 | 0.18 | [3]4,20 | [3]6,160 | no effect | 30 | 0.75 |
| [4]mKv3.1a CDNA (NGK2) | 0.1 | 0.6 | 1000 | n.d. | no effect | n.d. | n.d. |
| [5]rKv3.1 CDNA (Kv4) | 0.15 | 0.3 | n.d. | n.d. | no effect | n.d. | n.d. |
| Native channels | | | | | | | |
| [1]type 1 (human) | 0.12 | <0.1 | [3]10,20 | [3]5,50 | no effect | 30 | 0.76 |
| [6]type 1 (mouse) | 0.08 | <0.2 | [1,3]10,19 | [1,3]3,23 | no effect | 36 | 0.9 |
| [7]type n (human) | 8 | 0.19 | [1,3]13,24 | [1,3]6,18 | 3 | [1,*]28 | [1*]0.2 |
| [6]type n (mouse) | 10–13 | <0.2 | [1,3]9,17 | [1,3]7,28 | 3 | [1]40 | [1]0.27 | n.d. not determined
[1]data from this paper, numbers represent the mean of 3-5 determinations.
[2]The effect of 20 mM $Co^{2+}$ ca be described as a shift of the voltage dependence of channel activation ($\Delta E_n$) due to neutralizing negative surface charge and a direct blocking effect (gK(Co)/gK). Shift and block were assayed as described in DeCoursey, et al., 1985 and 1987.
[3]Quinine and verapamil increase the apparent rate of K+ channel inactivation, and produce "use-dependent" block suggesting a state-dependent block (DeCourse, et al., 1985). Because of the complex nature of block, the apparent blocking potency depends on the way it is measured. Therefore we gave two values for the apparent dissociation constant, $K_d$. The first value was calculated using the reduction of the integral under the current trace elicited by 200 ms depolarizing voltage steps from-80 mV to 40 mV, the second using the reduction of the peak current amplitude (compare DeCoursey, et al., 1987a).
[4]data from Yokoyama, et al., 1989
[5]data from Luneau, et al., 1991
[6]data from DeCoursey, et al., 1987
[7]data from DeCoursey, et al., 1984; Sands, et al., 1989 mKv3.1a (Yokoyama et al. (1989) ibid.) and rKv3.1b (Luneau et al. (1991) ibid.) gene products (Table II). The high degree of sensitivity to TEA is most likely due to the tyrosine (GDMYPQT) at the C-terminal end of the putative pore region (P-region) of the channel (MacKinnon and Yellen (1990) *Science* 250, 276; Kavanaugh et al. (1991) *J. Biol. Chem.* 266, 7583). In contrast, the Kv1.3 (type n) channel, with lower TEA sensitivity, has a histidine at the comparable position (Kavanaugh et al. (1991) ibid,).

A variety of other pharmacological agents were used to characterize the mKv3.1b gene product in the oocyte Single-channel Conductance: Measurements of single-channel conductance strengthen the identification of mKv3.1b as the gene which encodes the lymphocyte type 1 K+ channel. In an oocyte patch containing only two K+ channels, we measured single-channel currents by ramping the membrane potential from −80 to 80 mV within 450 ms every second (FIG. 13, left). Single-channel events can be seen at potentials more positive than −10 mV. The single-channel conductance of 27 pS was estimated from the slope of the current recorded during an opening (Table I). This value is similar to that reported for the cloned mKv3.1a channel (Yokoyama et al. (1989) ibid.; Table I), and the type 1 K+ channels in mouse lpr CD4−CD8− T cells (DeCoursey et al. (1987) ibid.), in normal cytotoxic cells (Lewis and Cahalan (1988) ibid.), and in human Louckes cells (Table I).

FIG. 13 (right) illustrates the effect of TEA on the slope conductance obtained from the same patch shown on the left. In the presence of 0.3 mM TEA, the apparent single-channel conductance was reduced to 9 pS, probably reflecting a fast, "flickery" block. The decrease of the unitary current corresponds fairly well to the reduction of macroscopic K+ current by TEA in a population of oocyte K+ channels following injection of mKv3.1b mRNA, as shown in FIG. 12. This suggests that rapid binding and release of TEA by the open pore account for the macroscopic block observed, a mechanism of block suggested for type n and type 1 K+ channels in lymphocytes.

Type 1 Channels in a Human Lymphoma Line: The human B cell lymphoma line, Louckes, has been reported to express large numbers of type 1 K+ channels (Shapiro and DeCoursey, (1988) Biophys. J. 53, 550a). We have confirmed that Louckes cells display a K+ channel with gating kinetics and pharmacological sensitivities indistinguishable from the type 1 K+ channels of mouse T cells (Table I and II). Because Louckes is a human cell line, it should be possible to compare the Kv3.1 transcripts isolated from these cells with Kv3.1 transcripts isolated from mouse T cells.

Kv3.1 mRNA in Mouse MRL-lpr T Cells and in Louckes Cells: We used PCR to amplify the hydrophobic core of the Kv3.1 coding region from mouse MRL-lpr T cells and from human Louckes cells; the Kv3.1a and Kv3.1b transcripts are identical in sequence in this region. Two oligonucleotide primers were prepared, one from the unique loop linking the S1 and S2 transmembrane helices (primer 1) (SEQ ID NO: 1) and the second from a region 112 bp downstream of the S6 transmembrane segment (primer 3) (SEQ ID NO: 3). We chose to make primers from these regions since their sequences are unique to Kv3.1, distinguishing it even from other closely related members of the Shaw-family, and because these primers flank the hydrophobic core that is common to both Kv3.1 transcripts. Kv3.1 specificity of these primers was confirmed by comparing their sequences with those available from GenBank. A third Kv3.1-primer (#3) was selected from the S5 transmembrane segment. These primers would be expected to amplify 774 bp (primers 1 and 3) (SEQ ID NOS: 1 and 3) and 390 bp (primers and 2) (SEQ ID NOS: 1 and 2) fragments, respectively, from Kv3.1.

Mouse and human lymphocytes that express type 1 K+ channels were used in our PCR experiments. The human B cell lymphoma line, Louckes, expresses many type 1 K+ channels (Shapiro and DeCoursey (1988) ibid.; Tables I and II), and abnormal lymph node CD4−CD8− cells from MRL-lpr mice, display ~200 type 1 K+ channels (Chandy et al. (1986) ibid). FIG. 14 shows that predicted 774 bp and 390 bp bands were amplified from mouse lpr CD4−CD8− T cells (lanes 1 and 2), and from human Louckes lymphoma cells (lanes 4 and 5). We were unable to amplify the predicted Kv3.1 bands from the mouse T cell line, EL4, that expresses type n, but not type 1 K+ channels (Cahalan et al. (1987) ibid.), although Kv1.3 (n channel) transcripts were detected (data not shown).

Further confirmation that these amplified fragments encoded Kv3.1 was obtained by DNA sequencing. The 669 bp fragment from human Louckes cells, hKv3.1, shares 93% sequence identity to the corresponding regions of mKv3.1a and rKv3.1b.

Since the PCR primers are contained in one exon, we may have inadvertently amplified the 774 bp and 390 bp fragments from genomic DNA contaminating the RNA sample. To control for this possibility we omitted the cDNA synthesis step (i.e., eliminated reverse transcriptase) and performed PCR directly on the RNA sample. Since Taq polymerase is a DNA-dependent polymerase, the predicted 774 bp fragment would be amplified if Kv3.1 genomic DNA was contaminating the RNA sample. The Kv3.1 band was not seen (data not shown), indicating that the fragments amplified by PCR represent legitimate Kv3.1 transcripts in mouse and human lymphocytes.

Chromosomal Localization of Kv3.1, Kv3.2, Kv1.1 and Isk Genes.

Genomic DNA from a panel of 59 human-Chinese hamster cell hybrids was hybridized to a 1.7kb EcoRI fragment of Kv3.1 at high stringency (65° C., 0.1×SSC) to avoid cross hybridization with related K+ channel genes (FIG. 17). Two Kv3.1-hybridizing bands are visible in human genomic DNA (lane 26) which is readily distinguishable from the one hybridizing band in hamster DNA (lane 1). The Kv3.1 probe only hybridized to genomic DNA from the hamster/human hybrid (HHW1049) in lane 12. This cell line contains human chromosomes 5 and 11. All other human chromosomes are represented in the panel. Eighteen hybrids contain either intact or derivative human chromosome 5. These data indicate that hKv3.1 is located on human chromosome 11. In parallel studies, we mapped the human chromosomal locations of three related K+ channel genes. Table III shows that the Shaker-related gene, Kv1.1 (Chandy et al. (1990) ibid.) and the Shaw-family gene Kv3.2 (McCormack et al. (1990) Proc. Natl. Acad. Sci. USA 87, 5227) are both located on human chromosome 12. The Isk gene encoding a slowly activating K+ channel (Takumi et al. (1988) Science 242, 1042; Murai et al. (1989) Biochem. Biophys. Res. Commun. 161, 176) was mapped to human chromosome 21.

TABLE III

Chromosomal localization
There is no discordancy in any of the 59 hamster-human cell hybrids between the presence of human chromosome 11 and hybridization with the mouse Kv3.1 probe (also see FIG. 8). Similarly, no discordancy was observed in any hybrid between the presence of chromosome 12 and hybridization with either the Kv3.2 or Kv1.1 probes. The Isk gene was similarly mapped to human chromosome 21.

| | Number of Discordant Hybrids for Chromosome: | | | | | | | | | | | | | | | | | | | | | | | |
|---|---|---|---|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | X | Y |
| Kv3.1 | 5 | 4 | 8 | 7 | 37 | 7 | 6 | 8 | 4 | 4 | 0 | 10 | 7 | 5 | 5 | 3 | 5 | 5 | 7 | 6 | 9 | 9 | 10 | 3 |
| Kv3.2 | 11 | 8 | 12 | 9 | 33 | 8 | 8 | 11 | 6 | 8 | 5 | 0 | 8 | 9 | 6 | 6 | 8 | 9 | 7 | 6 | 8 | 8 | 10 | 7 |
| Kv1.1 | 14 | 11 | 12 | 11 | 29 | 12 | 10 | 14 | 9 | 11 | 12 | 0 | 11 | 12 | 9 | 10 | 11 | 12 | 10 | 9 | 7 | 9 | 13 | 10 |

TABLE III-continued

Chromosomal localization
There is no discordancy in any of the 59 hamster-human cell hybrids between the presence of human chromosome 11 and hybridization with the mouse Kv3.1 probe (also see FIG. 8). Similarly, no discordancy was observed in any hybrid between the presence of chromosome 12 and hybridization with either the Kv3.2 or Kv1.1 probes. The Isk gene was similarly mapped to human chromosome 21.

| ISK | 10 | 12 | 11 | 11 | 31 | 12 | 11 | 16 | 12 | 12 | 10 | 8 | 10 | 13 | 9 | 9 | 13 | 11 | 9 | 10 | 0 | 9 | 14 | 11 |
|---|---|---|---|---|---|---|---|---|---|---|---|---|---|---|---|---|---|---|---|---|---|---|---|---|

Discussion

Studies with the patch clamp recording technique have revealed the presence of three distinct types of voltage-gated K+ channels in murine T cells (Chandy, et al., *Eur. J. Immunol.* 20, 747 (1990); Lewis and Cahalan, *Science* 239, 771 (1988); Grissmer, et al., *J. Immunol.* 141, 1137 (1988); Chandy, et al., *Science* 233., 1197 (1986)). These channels termed n, n' and l are distinguishable on the basis of biophysical and pharmacological criteria. Helper and cytotoxic T cells can be differentiated on the basis of their pattern of K+ channel expression $CD_4^+CD_8^-$ (helper) T cells display about 20-100 type n K+ channels whereas $CD_4^-CD_8^+$ (cytotoxic) T cells exhibit 20-200 type l K+ channels. Normal mitogen-activated T cells of all three subsets ($CD_4^+CD_8^-$, $CD_4^-CD_8^+$ and $CD_4^-CD_8^-$) express about 20-times more K+ channels than unstimulated cells, which are exclusively type n (22). Quiescent normal $CD_4^-CD_8^-$ T cells possess small numbers of one of these types of channels (Chandy, et al., *Eur. J. Immunol.* 20, 747 (1990); Grissmer, et al., *J. Immunol.* 141, 1137 (1988); Grissmer, et al., *J. Immunol.* 145, 2105 (1990)).

K+ channel expression was investigated in mAb-defined T cell subsets from mice with autoimmune diseases and control mice using the patch-clamp technique. We demonstrate that $CD_4^-CD_8^{31}$ cells from every murine model for SLE, type-1 diabetes, and chronic EAE and type II collagen arthritis display an abundance of type l K+ channels (FIG. 2). $CD_4^-CD_8^-$ T cells from normal strains of mice (FIGS. 1, 3, 4), or from mice immunized with heat killed *E. coli* or injected with CFA (FIG. 6), do not express this high level of type l K+ channels. The pattern of K+ channel expression in $CD_4^-CD_8^-$ T cells associated with autoimmunity is also dramatically different from that in normal mitogen-activated T cells and rapidly proliferating thymocytes which exhibit large numbers of type n K+ channels. Furthermore, the $CD_4^+CD_8^-$ (helper/inducer) and $CD_4^-CD_8^+$ (cyto-toxic/suppressor) cells from diseased mice display the same type and roughly the same number of K+ channels as their counterparts in normal mice. Thus, elevated expression of type l K+ channels appears to be a unique feature of $CD_4^-CD_8^-$ T cells associated with autoimmune disease.

Several lines of evidence indicate that $CD_4^-CD_8^-$ T cells contribute to the pathogenesis of autoimmunity. Increased numbers of $CD_4^-CD_8^-$ T cells are found both in humans and mice with SLE. These $CD_4^-CD_8^-$ T cells induce B cells from lupus-prone mice to secrete pathogenic cationic anti-DNA autoantibodies in vitro. Deposition of the cationic IgG anti-double-stranded autoantibodies of the negatively charged glomerular basement membrane results in inflammations and lupus nephritis. Severe lymphoproliferation of TcR $\alpha/\beta$ expressing $CD_4^-CD_8^-$ T cells in mice with the lpr or gld mutations is associated with the accelerated onset of SLE. These proliferating $CD_4^-CD_8^-$ T cells secrete B cell differentiation factors which may enhance autoantibody production. Increased numbers TcR $\gamma/\delta$-bearing $CD_4^-CD_8^-$ T cells have also been recently reported in the inflamed joints of patients with rheumatoid arthritis. The expansion of $CD_4^-CD_8^-$ T cells in autoimmune diseases seems to coincide with the appearance of $CD_4^+CD_8^-$ autoreactive T cells, suggesting a link between these two T cell populations. The demonstration that treatment with anti CD4 antibodies concomitantly reduces the $CD_4^-CD_8^-$ T cells population along with the $CD_4^-CD_8^-$ T cells in the lymphoid organs of MRL-lpr mice supports this conclusion. Anti-CD4 therapy also ameliorates the pathology of murine SLE type-1 diabetes, EAE collagen arthritis, and myasthenia gravis, suggesting that these autoimmune diseases share a dependence on autoreactive $CD_4^+$ cells and possibly $CD_4^-CD_8^-$ T cells.

Augmented type l K+ channel expression appears to be a valuable marker for $CD_4^-CD_8^-$ cells associated with murine SLE, type-1 diabetes mellitus and chronic EAE. These results focus attention on the possible role of $CD_4^-CD_8^-$ T cells in the pathogenesis of autoimmune diseases and emphasize the potential value of combining electrophysiological approaches with immunological and molecular techniques in the study of autoimmunity. Our results provide for exploiting the abundance of type l K+ channels in $CD_4^-CD_8^-$ T cells in testing the disease process. Investigation of the effects of type l K+ channel-specific drugs on the development of autoimmunity is made possible by this invention. Recent reports show that gamma/delta $CD_4^-CD_8^-$ T cells respond to mycobacterial antigens and accumulate in leprosy skin lesions, cutaneous leishmaniasis, and rheumatoid arthritic joints (Modlin, et al., *Nature* 339, 544 (1989); Holishitz, et al., *Nature* 339, 226 (1989)). By inducing the aggregation of monocytes, these $CD_4^-CD_8^-$ T cells may contribute to inflammatory processes (Modlin, et al., *Nature* 339, 544 (1989)). Alpha/beta TCR+ $CD_4^-CD_8^-$ T cells have been reported to act as helper cells, inducing autoreactive B cells to secrete pathogenic anti-DNA antibodies (Datta, et al., *J. Exp. Med.* 165, 1252 (1987); Sainis and Datta, *J. Immun.* 140, 2215 (1988)). $CD_4^-CD_8^-$ T cells have also been reported to abrogate oral tolerance (Kitamura, et al., *J. Immunol.* 139, 3251 (1987)). Collectively, these observations show that $CD_4^-CD_8^-$ T cells apparently have a significant role in biologically relevant immune responses and apparently are involved in the mechanisms that result in tissue damage found in autoimmune diseases. Activation via a pathway distinct from that triggered by mitogens or antigens (e.g., *E. coli* or CFA), may induce abundant expression of type l K+ channels on $CD_4^-CD_8^-$ T cells, regardless of the type of TCR they display on their cell surface.

Abundant type l K+ channel expression is a marker for $CD_4^-CD_8^-$ T cells associated with murine SLE, type-1 diabetes mellitus or chronic EAE; other T-cell subsets from mice with these autoimmune diseases retain their normal pattern of K+ channel expression.

Observations have been extended to mice with type II collagen arthritis, an autoimmune disorder that shares many immunological features with SLE, type-1 —diabetes and chronic EAE.

A substantially large fraction of CD4−CD8− T cells from mice with active type II collagen arthritis, display elevated numbers of type 1 K+ channels. In contrast, phenotypically similar cells from normal mice, or from mice immunized with CFA or heat-killed *E coli*, or mice inoculated with type II collagen without evidence of active disease, exhibit small numbers of K+ channels which may be types n, n′ or l. The pattern of K+ channel expression in helper (CD$_4$+CD$_8$−) and cytotoxic (CD$_4$−CD$_8$+) T cells from arthritic mice closely resemble that of their phenotypic equivalents in normal strains of mice. Thus, altered K+ channel expression appears to be a marker for CD4−CD8− T cells associated with four disparate autoimmune disorders.

This disclosure shows that the mouse Kv3.1 gene, when expressed in Xenopus oocytes, encodes a channel with properties remarkably similar to those of the l-type channel. Kv3.1 transcripts were found in T cells isolated from the lymph nodes of MRL-lpr mice with systemic lupus erythematosus, and in a human lymphoma cell line that also expresses the l-channel phenotype. By these criteria, it is concluded that Kv3.1 encodes the voltage-gated type 1 K+ channel in lymphocytes. The Kv3.1 gene maps to human chromosome 11; the related Kv1.1 and Kv3.2 genes are localized on human chromosome 12, while the IsK gene maps to human chromosome 21.

All of the various references cited herein are hereby expressly incorporated by reference herein.

The foregoing description details specific methods that can be employed to practice the present invention. Having detailed specific methods initially used to identify an etiological manifestation of autoimmune diseases, namely elevated type l ion channel expression in abnormal T cells, the art skilled will well enough know how to devise alternative reliable methods for arriving at the same basic information and for extending this information to other species including humans. Thus, however detailed the foregoing may appear in text, it should not be construed as limiting the overall scope hereof; rather, the ambit of the present invention is to be governed only by the lawful construction of the appended claims.

---

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

```
GAAATCGAGA AGCTTCGAAA CGG                                    23
```

( 2 ) INFORMATION FOR SEQ ID NO:2:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:2:

```
CAGGAAGATG ATCAGCTGCA GG                                     22
```

( 2 ) INFORMATION FOR SEQ ID NO:3:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

```
GTGTGGAGAG TTAACGACAG                                        20
```

(2) INFORMATION FOR SEQ ID NO:4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

```
AAAGTGCGTG TGCTCACTGG                                                    20
```

(2) INFORMATION FOR SEQ ID NO:5:

(i) SEQUENCE CHARACTERISTICS:
        (A) LENGTH: 696 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

```
TTCCTTACCT ACATCGAGGG CGTCTGTGTG GTCTGGTTCA CCTTCGAGTT CCTCATGCGT        60
GTCATCTTCT GCCCCAACAA GGTAGAGTTC ATCAAGAACT CGCTCAACAT CATTGACTTT       120
GTGGCCATCC TGCCCTTCTA CCTGGAGGTG GGGCTGAGCG CCTGTCCTC CAAGGCAGCC        180
AAGGACGTGC TGGGCTTCCT GCGCGTCGTC CGCTTCGTGC GCATCTTGCG CATCTTTAAG       240
CTGACCCGCC ACTTTGTGGG CCTGCGGGTC CTGGGCCACA CGCTCCGAGC CAGCACCAAC       300
GAGTTCCTGC TGCTCATCAT CTTCCTGGCC TTGGGCGTGC TGATCTTCGC CACCATGATC       360
TACTACGCCG AGAGGATAGG GGCACAGCCC AATGACCCCA GCGCCAGTGA GCACACGCAC       420
TTTAAGAACA TCCCCATCGG CTTCTGGTGG CCGTGGTCA CCATGACGAC CCTGGGCTAT        480
GGAGACATGT ACCCGCAGAC GTGGTCCGGC ATGCTGGTGG GGCTCTGTG TGCGCTGGCG        540
GGCGTGCTCA CCATCGCCAT GCCCGTGCCC GTCATCGTGA ACAATTTCGG GATGTATTAC       600
TCCTTAGCCA TGGCTAAGCA GAAACTACCA AAGAAAAAA AGAAGCATAT TCCGCGGCCA        660
CCGCAGCTGG GATCTCCCAA TTATTGTAAA TCTGTC                                 696
```

(2) INFORMATION FOR SEQ ID NO:6:

(i) SEQUENCE CHARACTERISTICS:
        (A) LENGTH: 1805 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

```
CCGCGGTCCT CTGTGCCCCC CGACGGCTGG GGGGAGGGGG GAAGAGGCCC TGCGCCCCC         60
TCCCCGTCGC CAACTCCCCC TGGCGGCAGC TCCCATGGGT GTCGCTGGGC CGCGCCATGC       120
CTAAGGGGGC GCCGCGATGG GCCAAGGGGA CGAGAGCGAG CGCATCGTGA TCAACGTGGG       180
CGGCACGCGC CACCAGACGT ACCGCTCGAC GCTGCGCACG CTGCCCGGCA CGCGGCTTGC       240
CTGGCTGGCA GAGCCGGACG CCCACAGCCA CTTCGACTAT GACCCGCGTG CCGACGAGTT       300
CTTCTTCGAC CGCCACCCGG GCGTCTTCGC TCACATCCTG AACTATTACC GCACCGGCAA       360
GCTTCACTGC CCGGCCGACG TGTGCGGGCC GCTCTACGAG GAGGAGCTGG CCTTCTGGGG       420
CATCGACGAG ACGGACGTGG AGCCCTGCTG CTGGATGACC TATCGCCAGC ACCGAGACGC       480
TGAGGAGGCG CTGGACAGCT TTGGCGGTGC GCCCTTGGAC AACAGCGCCG ACGACGCGGA       540
```

-continued

| | | | | | | |
|---|---|---|---|---|---|---|
| CGCCGACGGC | CCCGGCGACT | CGGGCGACGG | CGAGGACGAG | CTGGAGATGA | CCAAGAGATT | 600 |
| GGCACTCAGT | GACTCCCCAG | ATGGCCGGCC | TGGCGGCTTC | TGGCGCCGCT | GGCAACCGCG | 660 |
| CATCTGGGCG | CTGTTCGAGG | ACCCCTACTC | ATCCCGCTAC | GCGCGGTATG | TGGCCTTTGC | 720 |
| CTCCCTCTTC | TTCATCCTGG | TCTCCATCAC | AACCTTCTGT | CTGGAGACTC | ACGAGCGCTT | 780 |
| CAACCCCATC | GTGAACAAGA | CCGAAATCGA | GAACGTTCGA | AACGGCACCC | AAGTGCGGTA | 840 |
| CTACCGGGAA | GCAGAGACGG | AGGCCTTCCT | CACCTACATC | GAGGGCGTCT | GCGTGGTCTG | 900 |
| GTTCACCTTC | GAGTTCCTCA | TGCGTGTCGT | CTTCTGCCCC | AACAAGGTGG | AATTCATCAA | 960 |
| GAACTCCCTC | AATATCATTG | ACTTTGTGGC | CATTCTCCCC | TTCTACCTGG | AGGTGGGCCT | 1020 |
| AAGCGGCCTG | TCCTCAAAAG | CCGCCAAGGA | CGTTCTGGGC | TTCCTGCGCG | TCGTCCGCTT | 1080 |
| CGTGCGCATC | CTGCGCATCT | TCAAGCTGAC | CCGCCACTTC | GTGGGCCTGA | GGGTCCTGGG | 1140 |
| CCACACGCTC | CGTGCCAGCA | CCAACGAGTT | CCTGCTGCTT | ATCATCTTCC | TGGCCCTGGG | 1200 |
| AGTGCTCATC | TTTGCCACCA | TGATCTACTA | CGCCGAGAGG | ATAGGGGCAC | AGCCCAATGA | 1260 |
| CCCCAGCGCC | AGCGAACACA | CACACTTTAA | AAACATCCCC | ATCGGCTTCT | GGTGGGCTGT | 1320 |
| GGTCACCATG | ACGACACTGG | GCTATGGAGA | CATGTATCCC | CAGACGTGGT | CTGGAATGCT | 1380 |
| GGTGGGAGCC | TTGTGTGCTC | TGGCTGGTGT | GCTGACCATT | GCCATGCCGG | TGCCTGTCAT | 1440 |
| CGTGAACAAT | TTTGGGATGT | ACTACTCTTT | AGCCATGGCT | AAGCAGAAAC | TACCAAAGAA | 1500 |
| AAAAAAGAAG | CATATTCCGC | GGCCACCACA | GCTGGGATCT | CCCAATTATT | GTAAATCTGT | 1560 |
| CGTAAACTCT | CCACACCACA | GTACTCAGAG | TGACACATGC | CCGCTGGCCC | AGGAAGAAAT | 1620 |
| TTTAGAAATT | AACAGAGCAG | GTAGGAAACC | TCTCAGAGGC | ATGTCGATCT | GACCTTTCAC | 1680 |
| CTCCGCCCCC | TGTAGCAATG | ATTCCAGATC | CAGTCAGACT | GCTTCCTTAG | TTCCACGGGC | 1740 |
| GACCCAGGAT | CCTGTGCCCA | ACTTTGAGTT | GTGGAGCCTG | GGACCCCAGG | GAGATGCTGG | 1800 |
| GCGGC | | | | | | 1805 |

We claim:

1. An isolated DNA molecule having a sequence (SEQ ID NO:5) as set forth in FIG. 16.

2. A method of producing potassium channel protein comprising producing a double stranded DNA molecule having the sequence of claim 1, transforming a host cell with said double stranded DNA molecule in an expression vector and expressing the gene to produce the protein.

3. The product of the method according to claim 2.

4. The product according to claim 3 wherein said product is the human type 1 K+ channel.

5. An isolated DNA molecule having a sequence (SEQ ID NO: 6) as set forth in FIG. 15.

* * * * *

UNITED STATES PATENT AND TRADEMARK OFFICE
CERTIFICATE OF CORRECTION

PATENT NO. : 5,397,702                        Page 1 of 14
DATED : March 14, 1995
INVENTOR(S) : Cahalan, et al It is certified that error appears in the above-indentified patent and that said Letters Patent is hereby corrected as shown below:

Title page,
    Page 2, lefthand column, line 7, delete "#230.12" and insert therefor --#220.12--.

Column 1, line 12, following "1991," insert --now abandoned,--.

Column 1, line 14, following "1989," insert --now--.

Column 1, line 33, delete "type-1" and insert therefor --type 1--.

Column 2, line 51, delete "lpr or gld" and insert therefor --*lpr* or *gld*--.

Column 2, line 51, delete "supra" and insert therefor --supra--.

Column 2, line 67, delete "lpr" and insert therefor --*lpr*--.

Column 3, line 9, delete "supra" and insert therefor --supra--.

Column 3, line 13, delete "supra" and insert therefor --supra--.

Column 3, line 15, delete "lpr" and insert therefore --*lpr*--.

Column 3, line 17, delete "Supra" and insert therefor --supra--.

Column 3, line 18, delete "lpr and gld" and insert therefor --*lpr* and *gld*--.

UNITED STATES PATENT AND TRADEMARK OFFICE
CERTIFICATE OF CORRECTION

PATENT NO. : 5,397,702   Page 2 of 14
DATED : March 14, 1995
INVENTOR(S) : Cahalan, et al It is certified that error appears in the above-indentified patent and that said Letters Patent is hereby corrected as shown below:

Column 3, line 26, delete "lpr and gld" and insert therefor --*lpr* and *gld*--.

Column 4, line 18, delete "I" and insert therefor --1--.

Column 4, line 18, delete "type-1" and insert therefor --type 1--.

Column 4, line 34, preceding "materials" insert two indents.

Column 4, line 35, preceding "$K^+$" insert two indents.

Column 4, line 61, delete "in" and insert therefor --*in*--.

Column 4, line 62, delete "vitro" and insert therefor --*vitro*--.

Column 5, line 19, delete "supra" and insert therefor --supra--.

Column 5, line 27, delete "supra" and insert therefor --supra--.

Column 5, line 30, delete "supra" and insert therefor --supra--.

Column 6, line 18, delete "type-1" and insert therefor --type 1--.

Column 6, line 35, after "mice" delete --;--.

UNITED STATES PATENT AND TRADEMARK OFFICE
CERTIFICATE OF CORRECTION

PATENT NO. : 5,397,702            Page 3 of 14
DATED     : March 14, 1995
INVENTOR(S) : Cahalan, et al It is certified that error appears in the above-indentified patent and that said Letters Patent is hereby corrected as shown below:

Column 6, line 46, delete "lpr" and insert therefor --*lpr*--.

Column 6, line 46, delete "gld" and insert therefor --*gld*--.

Column 6, line 47, delete "lpr" and insert therefor --*lpr*--.

Column 6, line 53, delete "lprgld" and insert therefor --*lprgld*--.

Column 6, line 61, delete "cells" and insert therefor --T cells--.

Column 6, line 62, delete "type-1" and insert therefor --type 1--.

Column 7, line 39, after "mRNA" delete --.--.

Column 8, line 32, delete "lpr" and insert therefor --*lpr*--.

Column 9, line 39, delete "infra" and insert therefor --infra--.

Column 10, line 8, delete "Science" and insert therefor --*Science*--.

Column 10, line 12, delete "gld" and insert therefor --*gld*--.

Column 10, line 13, delete "lpr" and insert therefor --*lpr*--.

UNITED STATES PATENT AND TRADEMARK OFFICE
CERTIFICATE OF CORRECTION

PATENT NO. : 5,397,702  Page 4 of 14
DATED : March 14, 1995
INVENTOR(S) : Cahalan, et al It is certified that error appears in the above-indentified patent and that said Letters Patent is hereby corrected as shown below:

Column 10, line 26, delete "I" and insert therefor --1--.

Column 10, line 38, delete "$CD_8^+$" and insert therefor --$CD_8^-$--.

Column 10, line 41, delete "type-1" and insert therefor --type 1--.

Column 10, line 47, delete "type-1" and insert therefor --type 1--.

Column 10, line 49, delete "type-1" and insert therefor --type 1--.

Column 10, line 53, delete "type-1" and insert therefor --type 1--.

Column 10, line 56, delete "type-1" and insert therefor --type 1--.

Column 11, line 23, delete "type-1" and insert therefor --type 1--.

Column 11, line 35, delete "lpr" and insert therefor --*lpr*--.

Column 11, line 35, delete "gld" and insert therefor --*gld*--

Column 11, line 42, delete "type-1" and insert therefor --type 1--.

Column 11, line 64, delete "=" and insert therefor --≈--.

UNITED STATES PATENT AND TRADEMARK OFFICE
CERTIFICATE OF CORRECTION

PATENT NO. : 5,397,702
DATED : March 14, 1995
INVENTOR(S) : Cahalan, et al

It is certified that error appears in the above-indentified patent and that said Letters Patent is hereby corrected as shown below:

Column 12, line 21, delete "$CD_{8+}$" and insert therefor --$CD_8^+$--.

Column 12, line 23, delete "$1.2^+$" and insert therefor --$1.2^-$--.

Column 12, line 60, delete "supra" and insert therefor --supra--.

Column 12, line 65, delete "supra" and insert therefor --supra--.

Column 13, line 17, delete "supra" and insert therefor --supra--.

Column 13, line 18, delete "supra" and insert therefor --supra--.

Column 13, line 23, delete "supra" and insert therefor --supra--.

Column 13, line 40, delete "supra" and insert therefor --supra--.

Column 13, line 40, after "supra" delete --.--.

Column 13, line 41, delete "lpr" and insert therefor --*lpr*--.

Column 13, line 42, delete "gld" and insert therefor --*gld*--.

Column 14, line 20, delete "I" and insert therefor --1--.

UNITED STATES PATENT AND TRADEMARK OFFICE
CERTIFICATE OF CORRECTION

PATENT NO. : 5,397,702　　　　　　　　　　　　　Page 6 of 14
DATED　　　 : March 14, 1995
INVENTOR(S) : Cahalan, et al It is certified that error appears in the above-indentified patent and that said Letters Patent is hereby corrected as shown below:

Column 14, line 36, preceding "nels:" insert two indents.

Column 14, line 37, preceding "lated" insert two indents.

Column 14, line 38, preceding "described" insert two indents.

Column 14, line 39, preceding "Immunology" insert two indents.

Column 14, line 40, preceding "ments." insert two indents.

Column 14, line 41, preceding "type" insert two indents.

Column 14, line 42, preceding "as" insert two indents.

Column 14, line 43, preceding "channels." insert two indents.

Column 14, line 44, preceding "against" insert two indents.

Column 14, line 45, preceding "large" insert two indents.

Column 14, line 46, preceding "surface" insert two indents.

Column 14, line 47, preceding "antigens" insert two indents.

UNITED STATES PATENT AND TRADEMARK OFFICE
CERTIFICATE OF CORRECTION

PATENT NO. : 5,397,702                                          Page 7 of 14
DATED : March 14, 1995
INVENTOR(S) : Cahalan, et al It is certified that error appears in the above-indentified patent and that said Letters Patent is hereby corrected as shown below:

Column 14, line 48, preceding "ies" insert two indents.

Column 14, line 49, preceding "channels" insert two indents.

Column 14, line 49, delete "supra" and insert therefor --*supra*--.

Column 14, line 50, preceding "(b)" insert two indents.

Column 14, line 51, preceding "$K^+$" insert two indents.

Column 14, line 52, preceding "cell" insert two indents.

Column 14, line 53, preceding "presence" insert two indents.

Column 14, line 54, preceding "oisotope-," insert two indents.

Column 14, line 55, preceding "tach" insert two indents.

Column 14, line 56, preceding "rescence" insert two indents.

Column 14, line 57, preceding "radioactive" insert two indents.

Column 14, line 58, preceding "munosorbent" insert two indents.

UNITED STATES PATENT AND TRADEMARK OFFICE
CERTIFICATE OF CORRECTION

PATENT NO. : 5,397,702
DATED : March 14, 1995
INVENTOR(S) : Cahalan, et al

It is certified that error appears in the above-indentified patent and that said Letters Patent is hereby corrected as shown below:

Column 14, line 62, delete "supra" and insert therefor --*supra*--.

Column 14, line 63, delete "in vivo" and insert therefor --*in vivo*--.

Column 15, line 4, delete "supra" and insert therefor --*supra*--.

Column 15, line 4, delete "in" and insert therefor --*in*--.

Column 15, line 5, delete "vitro" and insert therefor --*vitro*--.

Column 15, line 18, delete "supra" and insert therefor --*supra*--.

Column 16, line 15, delete "CD4$^-$CD8$^-$" and insert therefor --CD4$^+$CD8$^-$--.

Column 17, line 31, preceding "cell" insert --T --.

Column 17, line 47, delete "MRL-lpr" and insert therefor --MRL-*lpr*--.

Column 17, line 47, delete "C3H-lpr" and insert therefor --C3H-*lpr*--.

Column 17, line 47, delete "gld" and insert therefor --*gld*--.

Column 17, line 48, delete "lprlgld" and insert therefor --*lprlgld*--.

UNITED STATES PATENT AND TRADEMARK OFFICE
CERTIFICATE OF CORRECTION

PATENT NO. : 5,397,702  
DATED : March 14, 1995  
INVENTOR(S) : Cahalan, et al

Page 9 of 14

It is certified that error appears in the above-indentified patent and that said Letters Patent is hereby corrected as shown below:

Column 17, line 52, preceding "and", delete "CD4⁻" and insert therefor --CD4⁺--.

Column 17, line 52, following "cytotoxic" delete "CD8⁻" and insert therefor --CD8⁺--.

Column 17, line 56, preceding "cells" insert --T --.

Column 17, line 60, preceding "cells" insert --T --.

Column 18, line 1, delete "lpr" and insert therefor --*lpr*--.

Column 18, line 3, preceding "cells" insert --T --.

Column 18, line 4, preceding "cells" insert --T --.

Column 18, line 6, delete "in vitro" and insert therefor --in vitro--.

Column 18, line 13, preceding "cells" insert --T --.

Column 18, line 14, delete "type-1" and insert therefor --type 1--.

Column 18, line 21, delete "type-1" and insert therefor --type 1--.

Column 18, line 23, preceding "cells" insert --T --.

UNITED STATES PATENT AND TRADEMARK OFFICE
CERTIFICATE OF CORRECTION

PATENT NO. : 5,397,702
DATED : March 14, 1995
INVENTOR(S) : Cahalan, et al

It is certified that error appears in the above-indentified patent and that said Letters Patent is hereby corrected as shown below:

Column 18, line 24, preceding "cells" insert --T --.

Column 18, line 26, preceding "cells" insert --T --.

Column 18, line 31, delete "/" and insert therefor --1--.

Column 18, line 31, preceding "cells" insert --T --.

Column 18, line 32, delete "type-1" and insert therefor --type 1--.

Column 18, line 43, preceding "cells" insert --T --.

Column 18, line 47, preceding "cells" insert --T --.

Column 18, line 48, delete "type-1" and insert therefor --type 1--.

Column 18, line 63, delete "8,3932" and insert therefor --88, 3932--.

Column 20, line 25, delete "lpr" and indert therefor --*lpr*--.

Column 20, line 27, delete "lpr" and indert therefor --*lpr*--.

Column 21, line 45, preceding "cells" insert --T --.

UNITED STATES PATENT AND TRADEMARK OFFICE
CERTIFICATE OF CORRECTION

PATENT NO. : 5,397,702
DATED : March 14, 1995
INVENTOR(S) : Cahalan, et al

It is certified that error appears in the above-indentified patent and that said Letters Patent is hereby corrected as shown below:

Column 21, line 48, preceding "cells" insert --T --.

Column 21, line 50, preceding "cells" insert --T --.

Column 21, line 56, preceding "cells" insert --T --.

Column 21, line 61, preceding "cells" insert --T --.

Column 21, line 67, preceding "cells" insert --T --.

Column 22, line 8, delete "$CD_8^-$" and insert therefor --$CD_8^+$--.

Column 22, line 13, preceding "cells" insert --T --.

Column 22, line 17, delete "in vivo" and insert therefor --in vivo--.

Column 22, line 19, preceding "cells" insert --T --.

Column 22, line 20, delete "in vivo" and insert therefor --in vivo--.

Column 22, line 21, preceding "cells" insert --T --.

Column 22, line 30, delete "in vitro" and insert therefor --in vitro--.

UNITED STATES PATENT AND TRADEMARK OFFICE
CERTIFICATE OF CORRECTION

PATENT NO. : 5,397,702

DATED : March 14, 1995

INVENTOR(S) : Cahalan, et al

It is certified that error appears in the above-indentified patent and that said Letters Patent is hereby corrected as shown below:

Column 22, line 34, preceding "cells in" insert --T --.

Column 22, line 37, preceding "cells" insert --T --.

Column 22, line 45, preceding "cells" insert --T --.

Column 22, line 65, preceding "cells" insert --T --.

Column 23, line 9 to 10, delete "Xenopus oocytes" and insert therefor --*Xenopus oocytes*--.

Column 25, line 21, delete "lpr" and insert therefor --*lpr*--.

Column 25, line 60, delete "GDMYPQT" and insert therefor --GDM$\underline{Y}$PQT--.

Column 26, line 15, delet3e "lpr" and insert therefor --*lpr*--.

Table II, line 9, delete "CDNA" and insert therefor --cDNA--.

Table II, line 10, delete "CDNA" and insert therefor --cDNA--.

Table II, line 11, delete "CDNA" and insert therefor --cDNA--.

UNITED STATES PATENT AND TRADEMARK OFFICE
CERTIFICATE OF CORRECTION

PATENT NO.   : 5,397,702
DATED        : March 14, 1995
INVENTOR(S)  : Cahalan, et al It is certified that error appears in the above-indentified patent and that said Letters Patent is hereby corrected as shown below:

Column 27, line 3, delete "lpr" and insert thererfor --*lpr*--.

Column 27, line 28, delete "human" and insert therefor --human--.

Column 27, line 31, delete "lpr" and insert thererfor --*lpr*--.

Column 27, line 34, delete "lpr" and insert thererfor --*lpr*--.

Column 28, line 2, preceding "cells" insert --T --.

Column 28, line 2, delete "lpr" and insert thererfor --*lpr*--.

Column 28, line 5, delete "lpr" and insert thererfor --*lpr*--.

Column 29, line 22, following "expression" insert --.--.

Column 29, line 37, delete "CD8$^{31}$" and insert therefor --CD8$^-$--.

Column 29, line 38, delete "type-1" and insert therefor --type 1--.

Column 29, line 62, delete "in vitro" and insert therefor --in vitro--.

Column 29, line 67, delete "lpr or gld" and insert therefor --*lpr* or *gld*--.

UNITED STATES PATENT AND TRADEMARK OFFICE
CERTIFICATE OF CORRECTION

PATENT NO. : 5,397,702
DATED : March 14, 1995
INVENTOR(S) : Cahalan, et al

It is certified that error appears in the above-indentified patent and that said Letters Patent is hereby corrected as shown below:

Column 30, line 20, delete "$CD4^-$" and insert therefor --$CD4^+$--.

Column 30, line 21, delete "lpr" and insert thererfor --*lpr*--.

Column 30, line 23, delete "type-1" and insert therefor --type 1--.

Column 30, line 28, preceding "cells" insert --T --.

Column 30, line 29, delete "type-1" and insert therefor --type 1--.

Column 30, line 40, preceding "Recent" insert an indent.

Column 31, line 20, delete "Xenopus" and insert therefor --*Xenopus*--.

Column 31, line 23, delete "lpr" and insert thererfor --*lpr*--.

Signed and Sealed this

Sixth Day of August, 1996

Attest:

BRUCE LEHMAN

*Attesting Officer*  *Commissioner of Patents and Trademarks*